US012758215B2

(12) United States Patent
Choi

(10) Patent No.: US 12,758,215 B2
(45) Date of Patent: Oct. 13, 2026

(54) METHOD AND APPARATUS FOR CONTROLLING SURGICAL INSTRUMENT

(71) Applicant: LIVSMED INC., Seongnam-si (KR)

(72) Inventor: Woo Jung Choi, Siheung-si (KR)

(73) Assignee: LIVSMED INC., Seongnam-si (KR)

( * ) Notice: Subject to any disclaimer, the term of this patent is extended or adjusted under 35 U.S.C. 154(b) by 0 days.

(21) Appl. No.: 18/999,228

(22) Filed: Dec. 23, 2024

(65) Prior Publication Data

US 2026/0060677 A1 Mar. 5, 2026

(30) Foreign Application Priority Data

Sep. 3, 2024 (KR) ........................ 10-2024-0119098

(51) Int. Cl.
*A61B 17/00* (2006.01)
*A61B 17/068* (2006.01)
*A61B 90/00* (2016.01)

(52) U.S. Cl.
CPC ............ *A61B 17/068* (2013.01); *A61B 90/08* (2016.02); *A61B 2017/00017* (2013.01);
(Continued)

(58) Field of Classification Search
CPC .................. A61B 17/068; A61B 90/08; A61B 2017/00017; A61B 2017/00398; A61B 2017/00477; A61B 2090/0807
(Continued)

(56) References Cited

U.S. PATENT DOCUMENTS 3,495,060 A * 2/1970 Biggs ...................... H01P 1/125 200/317
3,562,597 A * 2/1971 White .................. H01H 51/284 361/166
(Continued)

FOREIGN PATENT DOCUMENTS

CN 202434285 U * 9/2012
EP 3409216 A1 * 12/2018 ............. A61B 90/98
(Continued)

OTHER PUBLICATIONS

South Korea Ministry of Intellectual Property, "Request forthe Submission of an Opinion" issued for Korean Priority Application No. 10-2024-0119098 on Jun. 22, 2026.

*Primary Examiner* — Robert F Long
(74) *Attorney, Agent, or Firm* — Bridgeway IP Law Group, PLLC; Sang Ho Lee; Hyun Woo Shin

(57) ABSTRACT

Provided are a method and apparatus for controlling a surgical instrument. The surgical instrument includes an end tool including one or more jaws formed to be rotatable, a handle configured to control a motion of the end tool and detect a mounting of at least one component directly or indirectly connected thereto, and a connector formed to connect between the handle and the end tool through a first connection member and a second connection member, wherein the first connection member includes one end to which a first contact of the end tool is connected and another end to which a third contact of the handle is connected, and the second connection member includes one end to which a second contact of the end tool is connected and another end to which a fourth contact and a fifth contact of the handle are connected.

16 Claims, 24 Drawing Sheets

(52) U.S. Cl.
CPC ............... *A61B 2017/00398* (2013.01); *A61B 2017/00477* (2013.01); *A61B 2090/0807* (2016.02)

(58) Field of Classification Search
USPC ......... 227/175.1–182.1, 8, 19; 606/139, 142, 606/143, 205–208
See application file for complete search history.

(56) References Cited

U.S. PATENT DOCUMENTS

| | | | | | | |
|---|---|---|---|---|---|---|
| 3,922,513 | A | * | 11/1975 | Kravchuck | H01H 13/12 | 200/239 |
| 4,463,382 | A | * | 7/1984 | Pellegrini | H04N 5/44 | 348/706 |
| 4,699,445 | A | * | 10/1987 | Porta | H01R 13/11 | 439/830 |
| 4,772,225 | A | * | 9/1988 | Ulery | H01R 13/7195 | 333/182 |
| 5,002,501 | A | * | 3/1991 | Tucker | H01R 4/2433 | 439/417 |
| 5,529,235 | A | * | 6/1996 | Boiarski | A61B 90/98 | 600/101 |
| 5,971,801 | A | * | 10/1999 | Kato | H01R 13/62933 | 439/157 |
| 6,790,049 | B2 | * | 9/2004 | Kaylie | H05K 9/0056 | 333/100 |
| 7,830,225 | B2 | * | 11/2010 | Gale | H01R 24/547 | 333/136 |
| 8,862,209 | B2 | * | 10/2014 | Whitman | A61B 17/02 | 600/478 |
| 12,167,851 | B2 | * | 12/2024 | Hase | A61B 18/1445 | |
| 2010/0317214 | A1 | * | 12/2010 | Mulot | H01R 13/639 | 439/299 |
| 2018/0250002 | A1 | * | 9/2018 | Eschbach | A61B 17/0682 | |
| 2019/0298461 | A1 | * | 10/2019 | Holop | A61B 34/30 | |
| 2020/0155744 | A1 | * | 5/2020 | Tsoory | A61L 2/18 | |

FOREIGN PATENT DOCUMENTS

| | | | | | |
|---|---|---|---|---|---|
| JP | 10-2011-0010836 | A | | 2/2011 | |
| JP | 2022-153543 | A | | 10/2022 | |
| KR | 10-2023-0011283 | A | | 1/2023 | |
| KR | 10-2024-0015013 | A | | 2/2024 | |
| KR | 102729812 | B1 | * | 11/2024 | A61B 17/295 |
| WO | WO-2023237978 | A1 | * | 12/2023 | A61B 17/1155 |

* cited by examiner

METHOD AND APPARATUS FOR CONTROLLING SURGICAL INSTRUMENT

CROSS-REFERENCE TO RELATED APPLICATION

This application is based on and claims priority under 35 USC § 119 to Korean Patent Application No. 10-2024-0119098, filed on Sep. 3, 2024, in the Korean Intellectual Property Office, the disclosure of which is incorporated by reference herein in its entirety.

BACKGROUND

1. Field

The present disclosure relates to a method and apparatus for controlling a surgical instrument.

2. Description of the Related Art

Medically, surgery refers to the treatment of diseases by cutting, slitting, or manipulating the skin, mucous membranes, or other tissues using medical devices. In particular, open surgery, which cuts and opens the skin of a surgical site and cures, shapes, or removes an organ therein, may cause bleeding, side effects, patient pain, scars, or the like. Accordingly, recently, surgery performed by inserting only a medical device, for example, laparoscopic surgical instrument, microsurgical microscope, and the like by forming a predetermined hole in the skin or surgery using a robot has been spotlighted as an alternative.

Here, a surgical robot refers to a robot that has a function of replacing a surgical action performed by a surgeon. Advantageously, the surgical robot may operate more accurately and precisely as compared with a human and enable remote operation.

Surgical robots that are currently being developed worldwide may include a bone surgical robot, a laparoscopic surgical robot, a stereotactic surgical robot, and the like. Here, the laparoscopic surgical robot is a robot that performs minimum invasive surgery using a laparoscope and small surgical instruments.

Laparoscopic surgery is a cutting-edge surgery technique that involves perforating one or more small holes in the abdomen and inserting a laparoscope, which is an endoscope for looking inside the abdomen to perform the surgery, and is a field that is expected to advance in the future. Today's laparoscopes are mounted with computer chips and have been developed to the extent that magnified images, which are clearer than images seen with the naked eye, can be obtained and when used with specially-designed laparoscopic surgical tools while looking at a monitor screen, any type of surgery is possible.

Moreover, laparoscopic surgery offers the same range of surgical procedures as open surgery, but with several advantages including fewer complications, the ability to initiate treatment shortly after the procedure, and the capability to maintain the patient's stamina and immune functions. As a result, laparoscopic surgery is becoming increasingly recognized as the standard surgery for treating colorectal cancer or the like in places such as the United States and Europe.

Meanwhile, a surgical robot is generally composed of a master robot and a slave robot. When a surgical operator manipulates a control lever (e.g., a handle) equipped on the master robot, a surgical tool coupled to or held by a robot arm on the slave robot may be manipulated to perform surgery.

The aforementioned background technology is technical information possessed by the inventor for derivation of the present disclosure or acquired by the inventor during the derivation of the present disclosure, and is not necessarily prior art disclosed to the public before the application of the present disclosure.

SUMMARY

The present disclosure is directed to providing a method and apparatus for controlling a surgical instrument. The present disclosure is also directed to providing a computer-readable recording medium on which a program for executing the method on a computer is recorded.

The problem to be solved by the present disclosure is not limited to the problems mentioned above, and other problems and advantages of the present disclosure, which are not mentioned, will be understood by the following description, and will be more clearly understood by the embodiments of the present disclosure. In addition, it will be appreciated that the problems and advantages to be solved by the present disclosure may be realized by means and combinations thereof indicated in the claims.

Additional aspects will be set forth in part in the description which follows and, in part, will be apparent from the description, or may be learned by practice of the presented embodiments of the disclosure.

As a technical means for achieving the above-described technical problem, a first aspect of the present disclosure may provide a surgical instrument including an end tool including one or more jaws formed to be rotatable, a handle configured to control a motion of the end tool and detect a mounting of at least one component directly or indirectly connected thereto, and a connector formed to connect between the handle and the end tool through a first connection member and a second connection member, wherein the first connection member includes one end to which a first contact of the end tool is connected and another end to which a third contact of the handle is connected, and the second connection member includes one end to which a second contact of the end tool is connected and another end to which a fourth contact and a fifth contact of the handle are connected, wherein the handle transmits and receives information about at least one of the end tool and the connector based on a connection status of the first connection member, and detects whether at least one of the end tool and the connector is mounted based on a connection status of the second connection member.

The handle may determine whether the connector is mounted based on a closed loop formed by each of the fourth contact and the fifth contact being connected to the second connection member.

The connector may include a reuse prevention unit whose structure is deformed based on a pressure generated as the connector is mounted to or detached from the handle.

The connector may connect the second contact and the fifth contact to the same ground based on the connection status of the second connection member.

The information about the end tool may include at least one of a type of the end tool, a length of the end tool, whether the end tool is in use, a number of times the end tool has been used, and error information about the end tool.

The handle may transmit at least one of details of an error, a position of at least one member included in the end tool, and a current value input to at least one motor included in the surgical instrument to the end tool, based on whether the error has occurred in the end tool.

The first connection member may be formed to extend in a direction from the handle toward the end tool, the one end of the first connection member may include a sixth contact contactable with the first contact, the another end of the first connection member may include a seventh contact connected to the third contact, the second connection member may be formed to extend in the direction from the handle toward the end tool, the one end of the second connection member may include an eighth contact contactable with the second contact, and the another end of the second connection member may include a ninth contact contactable with the fourth contact and the fifth contact.

The one end and the another end of each of the first connection member and the second connection member may be formed to be inclined with respect to a plane perpendicular to the direction of extension.

The handle may include a sub-board disposed based on a distal end of the handle and connected to at least one of the third contact, the fourth contact and the fifth contact, and a main board connected to the sub-board and configured to control an operation of the surgical instrument.

The surgical instrument may further include a power generation unit that may include a motor pack including at least one motor, which is disposed to be at least partially accommodated in a housing of the handle and generates power for driving the end tool based on a signal input to the handle, and a roll drive motor configured generate power for roll-rotating the motor pack.

The surgical instrument may further include a power transmission unit including at least one wire that transmits the power generated from the power generation unit to the end tool.

A second aspect of the present disclosure may provide a connector formed to connect between a handle and an end tool through a first connection member and a second connection member, wherein the first connection member includes one end to which a first contact of the end tool is connected and another end to which a third contact of the handle is connected, and the second connection member includes one end to which a second contact of the end tool is connected and another end to which a fourth contact and a fifth contact of the handle are connected.

The second connection member may form a closed loop by being connected to each of the fourth contact and the fifth contact.

The connector may further include a reuse prevention unit whose structure is deformed based on a pressure generated as the connector is mounted to or detached from the handle.

The connector may connect the second contact and the fifth contact to the same ground based on a connection status of the second connection member.

The first connection member may be formed to extend in a direction from the handle toward the end tool, the one end of the first connection member may include a sixth contact contactable with the first contact, the another end of the first connection member may include a seventh contact connected to the third contact, the second connection member may be formed to extend in the direction from the handle toward the end tool, the one end of the second connection member may include an eighth contact contactable with the second contact, and the another end of the second connection member may include a ninth contact contactable with the fourth contact and the fifth contact.

The one end and the another end of each of the first connection member and the second connection member may be formed to be inclined with respect to a plane perpendicular to the direction of extension.

A third aspect of the present disclosure may provide a method of controlling a surgical instrument, the method including detecting whether at least one of an end tool and a connector is mounted based on a connection status of a second connection member, and transmitting and receiving information about at least one of the end tool and the connector based on a connection status of a first connection member, wherein the end tool includes one or more jaws formed to be rotatable, the connector is formed to connect between a handle and the end tool through a first connection member and a second connection member, wherein the first connection member includes one end to which a first contact of the end tool is connected and another end to which a third contact of the handle is connected, and the second connection member includes one end to which a second contact of the end tool is connected and another end to which a fourth contact and a fifth contact of the handle are connected, and the handle controls a motion of the end tool and detects a mounting of one or more components directly or indirectly connected thereto.

In addition, other methods and systems for implementing the present disclosure, and a computer-readable recording medium on which a program for executing the method on a computer is recorded may be further provided.

Other aspects, features, and advantages other than those described above will become apparent from the following drawings, claims, and detailed description of the disclosure.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
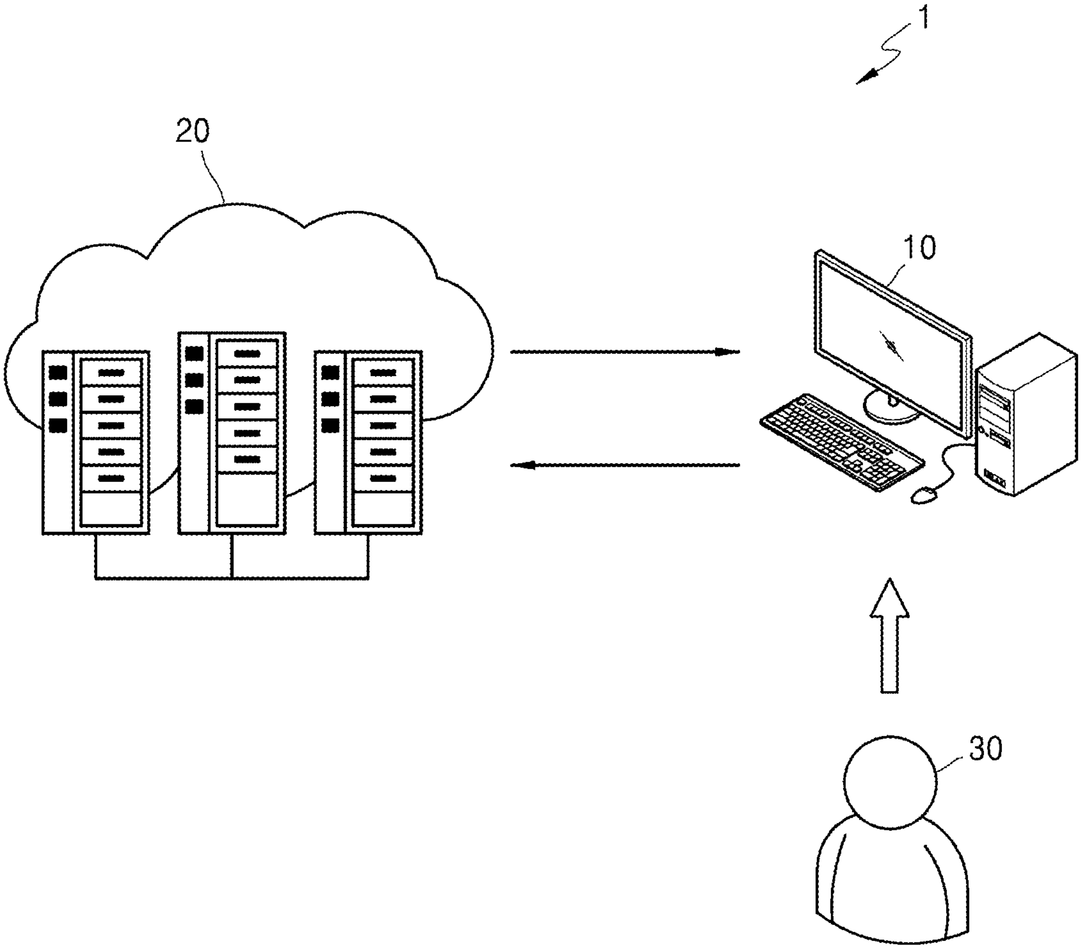
FIG. 1 is a diagram for describing an example of a system for driving a surgical instrument according to an embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

Hereinafter, various embodiments of the present disclosure are described with reference to the accompanying drawings. While the present disclosure is susceptible to various modifications and may have several embodiments, specific embodiments thereof are shown by way of example in the drawings and will herein be described in detail. However, it should be understood that there is no intent to limit the present disclosure to the specific embodiments, but on the contrary, the present disclosure is to cover all modifications, equivalents, and alternatives falling within the spirit and scope of the present disclosure. With regard to description of the drawings, like reference numerals have been used for like components.

Expressions such as "includes" or "may include" that may be used in various embodiments of the present disclosure indicate the existence of a corresponding function, operation, or component that is disclosed, and are not intended to limit one or more additional functions, operations, or components. In addition, in the various embodiments of the present disclosure, it is to be understood that the terms such as "including," "having," and the like are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

In various embodiments of the present disclosure, the expression "or" includes any and all combinations of one or more of the associated listed items. For example, "A or B" may include "A," "B," or "both A and B."

While expressions such as "first" and "second" used in the various embodiments of the present disclosure may describe various components of the various embodiments, the corresponding components are not limited by the expressions such as "first" and "second." For example, these expressions do not limit the order and/or importance of corresponding components. These expressions may be used to distinguish one component from another. For example, both a first user device and a second user device are user devices and indicate different user devices. For example, a first component may be named a second component or a second component may be named a first component without departing from the scope of the various embodiments of present disclosure.

In an embodiment of the present disclosure, the terms "module," "unit," "part," or the like are terms which designate a component that performs at least one function or operation, and the component may be implemented with a hardware or software, or a combination of hardware and software. In addition, a plurality of "modules," a plurality of "units," or a plurality of "parts", except for "a module," "a unit," or a "part" which needs to be implemented to a specific hardware, may be integrated to at least one module or a chip and implemented in at least one processor.

The terms used in various embodiments of the present disclosure are used to describe a particular embodiment only and are not intended to limit the various embodiments of the present disclosure. Singular forms are intended to include plural forms as well, unless the context clearly indicates otherwise.

Unless otherwise defined, all terms used herein, including technical or scientific terms, have the same meanings as those generally understood by those with ordinary knowledge in the field of art to which the various embodiments of the present disclosure belongs.

Generally used terms defined in a dictionary should be interpreted to have meanings the same as meanings in the context of the related art and are not interpreted as ideal or excessively formal meanings unless the various embodiments of the present disclosure clearly define otherwise.

Hereinafter, various embodiments of the present disclosure will be described in detail with reference to the accompanying drawings.

FIG. 1 is a diagram for describing an example of a system for driving a surgical instrument according to an embodiment.

Referring to FIG. 1, a system 1 includes a user terminal 10 and a server 20. For example, the user terminal 10 and the server 20 may be connected by a wired or wireless communication method to transmit and receive data (e.g., information about an operation unit, whether an error has occurred in the operation unit, or the like) to and from each other.

For convenience of description, in FIG. 1, the system 1 is illustrated as including the user terminal 10 and the server 20, but the present disclosure is not limited thereto. For example, the system 1 may include another external device (not shown), and operations of the user terminal 10 and the server 20 to be described later may be implemented by a single device (e.g., the user terminal 10 or the server 20) or a plurality of devices.

The user terminal 10 may include a display device and a device for receiving user input (e.g., a keyboard, a mouse, or the like), and may be a computing device including a memory and a processor. For example, the display device may be implemented as a touch screen and may receive user input. For example, the user terminal 10 may correspond to a notebook personal computer (PC), a desktop PC, a laptop computer, a tablet computer, a smartphone, and the like, but the present disclosure is not limited thereto.

Meanwhile, the user terminal 10 may be a surgical instrument. As an example, the user terminal 10 may be a surgical instrument including a memory and a processor. As another example, the user terminal 10 may be a manipulation unit including a memory and a processor. However, examples of the user terminal 10 are not limited to those described above.

The server 20 may be a device that communicates with an external device (not shown) including the user terminal 10. As an example, the server 20 may be a device that stores information about the operation unit, whether an error has occurred in the operation unit, details of the error, the position of at least one member included in the operation unit, a current value input to at least one motor included in the surgical instrument, and the like.

Alternatively, the server 20 may be a computing device that includes a memory and a processor and has its own computing capabilities. As an example, the server 20 may perform at least some of operations of the user terminal 10 to be described later with reference to FIGS. 1 to 17. For example, the server 20 may be a cloud server, but the present disclosure is not limited thereto.

The user terminal 10 may determine whether a connector is mounted based on a connection status of at least one connection member included in the connector, or may write or read information about the operation unit. For example, the user terminal 10 may determine whether the connector is mounted based on a connection status of a second connection member, and may write information about the operation unit or have the manipulation unit read the information, based on a connection status of a first connection member. The operation unit may include a first contact performing a communication operation and a second contact performing a ground operation. The manipulation unit may include a third contact performing a communication operation, a fourth contact performing a ground operation, and a fifth contact performing a mounting detection operation. The connector may include the first connection member connected to the first contact and the third contact. Further, the connector may include the second connection member connected to the second contact, the fourth contact, and the fifth contact.

According to an embodiment, the user terminal 10 may write information about the operation unit to the operation unit or have the manipulation unit read the information, based on the connection status of the first connection member. The information about the operation unit may include at least one of a type of the operation unit, a length of the operation unit, whether the operation unit is in use, the number of times the operation unit has been used, and error information about the operation unit.

According to an embodiment, the user terminal 10 may write at least one of the details of the error, the position of at least one member included in the operation unit, and the current value input to at least one motor included in the surgical instrument to the operation unit based on whether an error has occurred in the operation unit.

The user terminal 10 according to an embodiment may receive information about the operation unit from at least one of a main board and the operation unit based on a sub-board. The sub-board is disposed based on a distal end of the manipulation unit and may be connected to at least one of the third contact, the fourth contact, and the fifth contact. The main board may be connected to the sub-board to control the operation of the surgical instrument.

The user terminal 10 according to an embodiment may determine whether a drape is mounted based on a closed loop formed by each of the fourth contact and the fifth contact being connected to the second connection member.

Meanwhile, for convenience of description, throughout the description, it has been described that the user terminal 10 determines whether the connector is mounted based on the connection status of the second connection member, and writes information about the operation unit and has the manipulation unit read the information based on the connection status of the first connection member, but the present disclosure is not limited thereto. For example, at least some of operations performed by the user terminal 10 may be performed by the server 20.

In other words, at least some of operations of the user terminal 10 to be described with reference to FIGS. 1 to 17 may be performed by the server 20. For example, the server 20 may determine whether at least one of the operation unit and the connector is mounted based on the connection status of the second connection member. In addition, the server 20 may write information about at least one of the operation unit and the connector and have the manipulation unit read the information, based on the connection status of the first connection member.

Figure 2A:
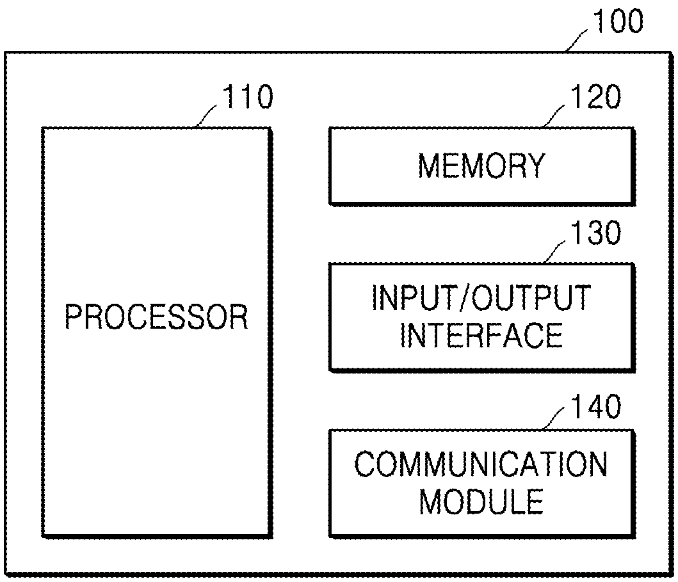
FIG. 2A is a configuration diagram illustrating an example of a user terminal according to an embodiment.

FIG. 2A is a configuration diagram illustrating an example of a user terminal according to an embodiment.

Referring to FIG. 2A, a user terminal 100 includes a processor 110, a memory 120, an input/output interface 130, and a communication module 140. For convenience of description, only components related to the present disclosure are illustrated in FIG. 2A. Accordingly, other general-purpose components in addition to the components illustrated in FIG. 2A may be further included in the user terminal 100. In addition, it will be apparent to those skilled in the art related to the present disclosure that the processor 110, the memory 120, the input/output interface 130, and the communication module 140 illustrated in FIG. 2A may be implemented as independent devices.

The processor 110 may process instructions of a computer program by performing a basic arithmetic operation, a logic operation, and an input/output operation. Here, the instructions may be provided from the memory 120 or an external device (e.g., the server 20 or the like). In addition, the processor 110 may control overall operations of the other components included in the user terminal 100.

The processor 110 may determine whether at least one of the end tool and the connector is mounted based on the connection status of the second connection member. For example, the processor 110 may determine that the connector is mounted on the manipulation unit when the second connection member is in a state of being connected to each of the fourth contact and the fifth contact.

In addition, the processor 110 may write information about the operation unit or have the manipulation unit read the information, based on the connection status of the first connection member. For example, the processor 110 may write information about the operation unit to the operation unit or have the manipulation unit read the information, when the first connection member is in a state of being connected to each of the first contact and the fourth contact.

Further, the processor 110 may write at least one of the details of the error, the position of at least one member included in the operation unit, and the current value input to at least one motor included in the surgical instrument to the operation unit based on whether an error has occurred in the operation unit.

In addition, the processor 110 may receive information about the operation unit from at least one of a main board and the operation unit based on a sub-board. Here, the sub-board is disposed based on a distal end of the manipulation unit and may be connected to at least one of the third contact, the fourth contact, and the fifth contact. Here, the main board may be connected to the sub-board to control the operation of the surgical instrument.

In addition, the processor 110 may determine whether the connector is mounted based on a closed loop formed by each of the fourth contact and the fifth contact being connected to the second connection member.

Specific examples in which the processor 110 according to an embodiment operates will be described with reference to FIGS. 3 to 17.

The processor 110 may be implemented in an array of multiple logic gates, or in a combination of a universal microprocessor and a memory that stores a program executable in the microprocessor. For example, the processor 110 may include a general-purpose processor, a central processing unit (CPU), a microprocessor, a digital signal processor (DSP), a controller, a microcontroller, a state machine, or the like. In some environments, the processor 110 may include an application-specific semiconductor (ASIC), a programmable logic device (PLD), a field programmable gate array (FPGA), or the like. For example, the processor 110 may refer to a combination of processing devices such as, for example, a combination of a DSP and a microprocessor, a combination of a plurality of microprocessors, a combination of one or more microprocessors in conjunction with a DSP core, or a combination of any other such configuration.

The memory 120 may include any non-transitory computer-readable recording medium. In an example, the memory 120 may include a permanent mass storage device such as a random access memory (RAM), a read-only memory (ROM), a disk drive, a solid state drive (SSD), a flash memory, or the like. In another example, the permanent mass storage device such as a ROM, SSD, a flash memory, a disk drive, or the like may be a separate permanent storage device which is distinguishable from the memory. In addition, an operating system (OS) and at least one program code (e.g., a code for the processor 110 to perform operations to be described later with reference to FIGS. 3 to 17) may be stored in the memory 120.

These software components may be loaded from a computer-readable recording medium separate from the memory 120. The separate computer-readable recording medium may be a recording medium that may be directly connected to the user terminal 100, and may include, for example, a computer-readable recording medium, such as a floppy drive, a disk, a tape, a DVD/CD-ROM drive, a memory card, or the like. Alternatively, the software components may be loaded into the memory 120 through the communication module 140 instead of the computer-readable recording medium. For example, at least one program may be loaded into the memory 120 based on a computer program (e.g., a computer program for performing, by the processor 110, operations to be described later with reference to FIGS. 3 to 13) installed by the files provided through the communication module 140 by developers or a computer file distribution system that distributes the installation files of applications.

The input/output interface 130 may be a member for an interface with a device (e.g., a keyboard, a mouse, or the like) for input or output, the member being connected to the user terminal 100 or being included in the user terminal 100. The input/output interface 130 may be configured separately from the processor 110, but the present disclosure is not limited thereto, and the input/output interface 130 may be configured to be included in the processor 110.

The communication module 140 may provide a configuration or a function for the server 20 and the user terminal 100 to communicate with each other through a network. In addition, the communication module 140 may provide a configuration or function for the user terminal 100 to communicate with another external device. For example, a control signal, a command, data, or the like, which is provided according to the control of the processor 110, may be transmitted to the server 20 and/or an external device through the communication module 140 and the network.

Meanwhile, although not shown in FIG. 2A, the user terminal 100 may further include a display device. For example, the display device may be implemented as a touch screen. Alternatively, the user terminal 100 may be connected to an independent display device through a wired or wireless communication method to transmit/receive data to or from each other. For example, information about the operation unit, whether an error has occurred in the operation unit, or the like may be provided through the display device.

Figure 2B:
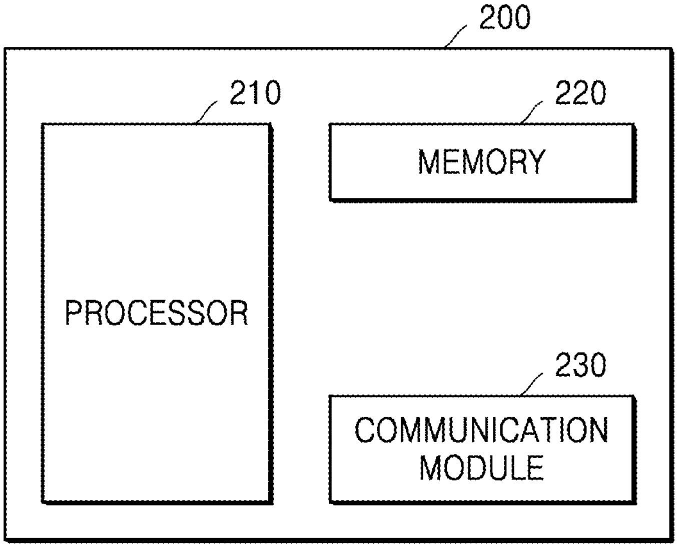
FIG. 2B is a configuration diagram illustrating an example of a server according to an embodiment.

FIG. 2B is a configuration diagram illustrating an example of a server according to an embodiment.

Referring to FIG. 2B, a server 200 includes a processor 210, a memory 220, and a communication module 230. For convenience of description, only components related to the present disclosure are illustrated in FIG. 2B. Accordingly, other general-purpose components other than the components illustrated in FIG. 2B may be further included in the server 200. In addition, it will be apparent to those skilled in the art related to the present disclosure that the processor 210, the memory 220, and the communication module 230 illustrated in FIG. 2B may be implemented as independent devices.

The processor 210 may detect whether at least one of the end tool and the connector is mounted based on the connection status of the second connection member. In addition, the processor 210 may transmit and receive information about at least one of the end tool and the connector based on the connection status of the first connection member.

In other words, at least one of the operations of the processor 110 described above with reference to FIG. 2A may be performed by the processor 210. In this case, the user terminal 100 may output information, which is transmitted from the server 200, through the display device.

Meanwhile, an implementation example of the processor 210 is the same as the implementation example of the processor 110 described above with reference to FIG. 2A, and thus a detailed description thereof will be omitted.

Various data such as data necessary for an operation of the processor 210 and data generated according to the operation of the processor 210 may be stored in the memory 220. In addition, an operating system (OS) and at least one program (e.g., a program necessary for the operation of the processor 210, or the like) may be stored in the memory 220.

Meanwhile, an implementation example of the memory 220 is the same as the implementation example of the memory 120 described above with reference to FIG. 2A, and thus a detailed description thereof will be omitted.

The communication module 230 may provide a configuration or a function for the server 200 and the user terminal 100 to communicate with each other through a network. In addition, the communication module 230 may provide a configuration or function for the server 200 to communicate with another external device. For example, a control signal, a command, data, or the like, which is provided according to the control of the processor 210, may be transmitted to the user terminal 100 and/or an external device through the communication module 230 and the network.

Figure 3:
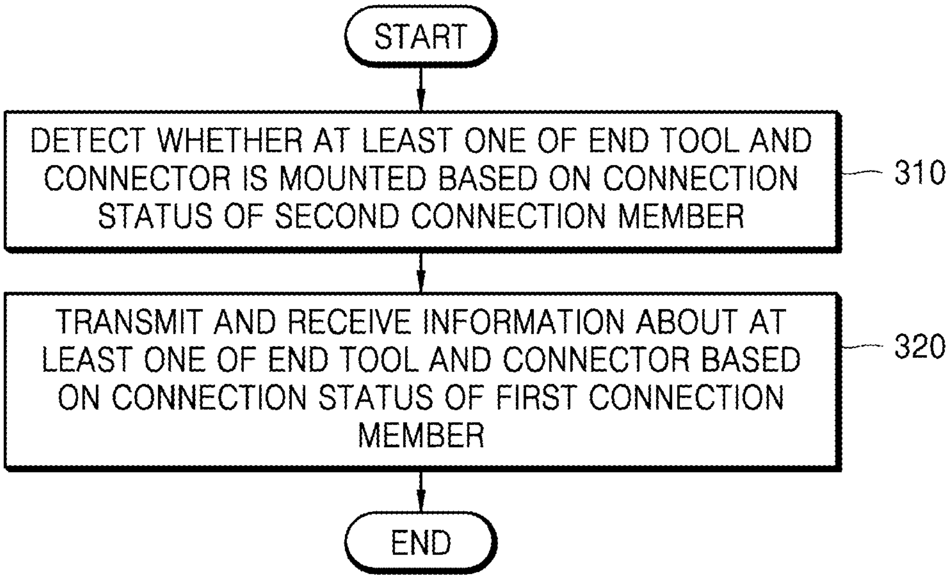
FIG. 3 is a flowchart for describing an example of a method of controlling a surgical instrument according to an embodiment.

FIG. 3 is a flowchart for describing an example of a method of controlling a surgical instrument according to an embodiment.

Referring to FIG. 3, the method of controlling a surgical instrument includes operations that are processed in time series by the user terminal 10 or 100 or the processor 110 illustrated in FIGS. 1 and 2A. Thus, the contents described above regarding the user terminal 10 or 100 or the processor 110 illustrated in FIGS. 1 and 2A may also be applied to the method of controlling a surgical instrument of FIG. 3, even when omitted below.

In addition, as described above with reference to FIGS. 1 and 2B, at least one of the operations of the method of controlling a surgical instrument of FIG. 3 may be processed by the server 20 or 200 or the processor 210.

In operation 310, the processor 110 may detect whether at least one of the end tool and the connector is mounted based on a connection status of the second connection member. For example, the processor 110 may determine that the connector is mounted on the manipulation unit when the second connection member is in a state of being connected to each of the fourth contact and the fifth contact.

In operation 320, the processor 110 may transmit and receive information about at least one of the end tool and the connector based on a connection status of the first connection member. As an example, the processor 110 may write information about the operation unit to the operation unit or have the manipulation unit read the information, when the first connection member is in a state of being connected to each of the first contact and the third contact. As another example, the processor 110 may write information about the connector or have the manipulation unit read the information, based on a connection status of the first connection member. The processor 110 may write information about the connector or have the manipulation unit read the information, when the first connection member is in a state of being connected to the third contact. The information about the connector may include whether the connector is in use, the number of times the connector has been used, and the like, but the present disclosure is not limited thereto.

As an example, the processor 110 may have the manipulation unit read the type of the operation unit, the length of the operation unit, whether the operation unit is in use, the number of times the operation unit has been used, and error information about the operation unit, based on the connection status of the first connection member. The error information about the operation unit may include information about past errors of the operation unit recorded in the operation unit.

As another example, the processor 110 may write information about whether the operation unit is in use, the number of times the operation unit has been used, and error information about the operation unit to the operation unit, based on the connection status of the first connection member.

Through the above-described examples, a method has been described in which the processor 110 writes information about the operation unit or has the manipulation unit read the information, based on the connection status of the first connection member, but the present disclosure is not limited thereto.

Meanwhile, the processor 110 may write at least one of the details of the error, the position of at least one member included in the operation unit, and the current value input to at least one motor included in the surgical instrument to the operation unit based on whether an error has occurred in the operation unit. The information written to the operation unit may be read by the manipulation unit again under the control of the manipulation unit. In addition, the information written to the operation unit may be read by another manipulation unit under the control of the another manipulation unit when the operation unit is detached from the manipulation unit and then mounted on the another manipulation unit.

In addition, the processor 110 may receive information about the operation unit from at least one of the main board and the operation unit based on the sub-board. Here, the sub-board is disposed based on the distal end of the manipulation unit and may be connected to at least one of the third contact, the fourth contact, and the fifth contact. Here, the main board may be connected to the sub-board to control the operation of the surgical instrument.

In addition, the processor 110 may determine whether the connector is mounted based on a closed loop formed by each of the fourth contact and the fifth contact being connected to the second connection member.

Figure 4:
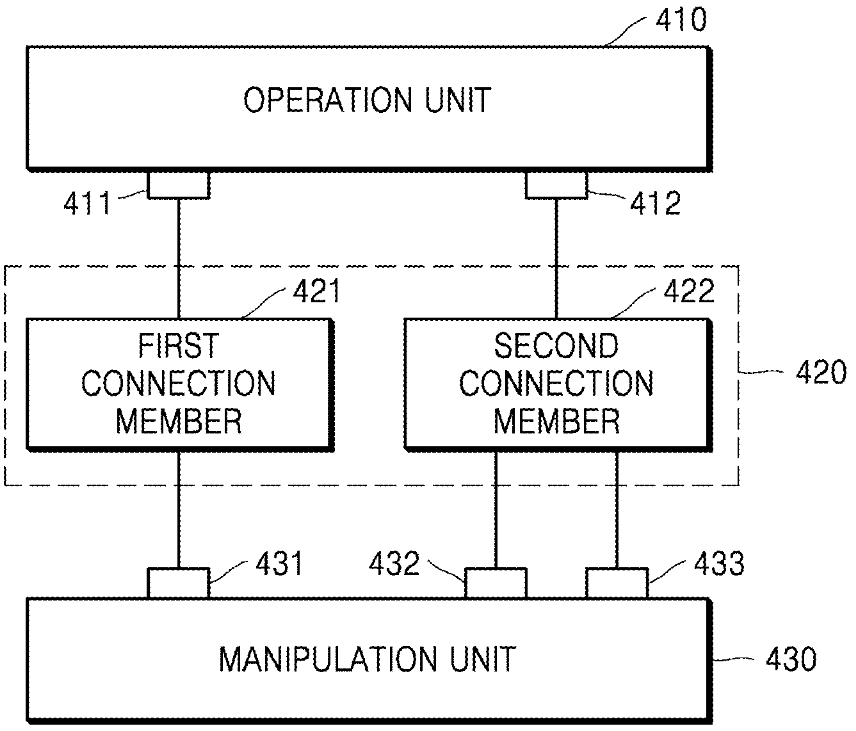
FIG. 4 is a diagram for describing another example of the system for driving a surgical instrument according to an embodiment.

FIG. 4 is a diagram for describing another example of the system for driving a surgical instrument according to an embodiment.

The system includes an operation unit 410, a connector 420, and a manipulation unit 430. For example, the operation unit 410 and the manipulation unit 430 may be connected by a wired or wireless communication method to transmit and receive data (e.g., information about an operation unit, whether an error has occurred in the operation unit, or the like) to and from each other. Alternatively, the operation unit 410 and the manipulation unit 430 may be connected by being mounted on the connector 420 to transmit and receive data (e.g., information about the operation unit, whether an error has occurred in the operation unit, and the like) to and from each other.

For convenience of description, in FIG. 4, it is illustrated that the operation unit 410, the connector 420, and the manipulation unit 430 are included in the system, but the present disclosure is not limited thereto. For example, the system may include other external devices (not shown).

The operation unit 410 may perform motions necessary for surgery under the control of the manipulation unit 430. For example, the operation unit 410 may include an end tool, a power transmission unit, and the like.

The operation unit 410 may include contacts that may be attached and connected to the connector 420. The operation unit 410 may include a first contact performing a communication operation and a second contact performing a ground operation. A first contact 411 may be connected to the connector 420 and may perform a communication operation so that the operation unit 410, the connector 420, and the manipulation unit 430 can transmit and receive data to and from each other. A second contact 412 may be connected to the connector 420 and may perform a ground operation so that a circuit inside the operation unit 410 may be connected to the ground. For example, the second contact 412 may be connected to the connector 420, which in turn is connected to the manipulation unit 430, allowing the second contact 412 to be connected to the ground included in the manipulation unit 430 or to the ground connected to the manipulation unit 430.

The connector 420 is mounted to the operation unit 410 and/or the manipulation unit 430, enabling the manipulation unit 430 to perform a detection or communication operation. For example, the connector 420 may include a first connection member 421 connected to the first contact 411 and a third contact 431, and a second connection member 422 connected to the second contact 412, a fourth contact 432, and a fifth contact 433. The first connection member and the second connection member may be members having the shape of a plate, a rod, a wire, a block, or the like, and are not limited to the examples described above.

Meanwhile, the connector 420 may perform an operation of covering an outer surface of the operation unit 410 and/or the manipulation unit 430 to protect the operation unit 410 and/or the manipulation unit 430 from contamination or the like. For example, the connector 420 may include a drape that covers the outer surface of the operation unit 410 and/or the manipulation unit 430.

Although not shown in FIG. 4, the first connection member may include a sixth contact connected to the first contact and a seventh contact connected to the third contact. In addition, the second connection member may include an eighth contact connected to the second contact and a ninth contact connected to the fourth contact and/or the fifth contact.

The manipulation unit 430 may be a handle that performs an operation to detect a mounting of the operation unit 410 and/or the connector 420, or performs an operation to communicate with the operation unit 410. For example, the manipulation unit 430 may control the motions of the end tool and detect the mounting of one or more components directly or indirectly connected to the manipulation unit 430. Here, the one or more components directly or indirectly connected to the manipulation unit 430 may include a component (e.g., the connector 420) that is directly coupled to the manipulation unit 430, or may include a component (e.g., the operation unit 410) that is indirectly coupled to the manipulation unit 430.

The manipulation unit 430 may include the third contact performing a communication operation, the fourth contact performing a ground operation, and the fifth contact performing a mounting detection operation. For example, the manipulation unit 430 may include a component for a user to input signals to control the operation of the operation unit 410. The manipulation unit 430 may read information about the operation unit 410 (e.g., a type of the operation unit 410, a length of the operation unit 410, whether the operation unit 410 is in use, the number of times the operation unit 410 has been used, error information about the operation unit 410, and the like). or write updated information about the operation unit 410 (e.g., whether the updated operation unit 410 is in use, the number of times the operation unit 410 has been used, error information about the updated operation unit 410, and the like) to the operation unit 410.

The manipulation unit 430 may determine whether the connector 420 is mounted, based on a connection status of the second connection member 422. For example, the manipulation unit 430 may determine whether the connector 420 is mounted based on a closed loop formed by the second connection member 422 included in the connector 420 being connected to the fourth contact 432 and the fifth contact 433 that are included in the manipulation unit 430.

In addition, the manipulation unit 430 may write or read information about the operation unit 410 based on a connection status of the first connection member 421. For example, as the first contact 411 included in the operation unit 410 is connected to the first connection member 421 and the third contact 431 included to in the manipulation unit 430 is connected to the first connection member 421, the manipulation unit 430 can write or read information about the operation unit 410.

Meanwhile, the connector 420 may perform an operation of connecting the operation unit 410 and the manipulation unit 430 to the same ground based on the connection status of the second connection member 422. For example, as the connector 420 is connected to the second contact 412, the fourth contact 432, and the fifth contact 433, the operation unit 410 and the manipulation unit 430 may be connected to the same ground.

Meanwhile, the manipulation unit 430 may write error information to the operation unit 410 based on whether an error has occurred in the operation unit 410. When an error occurs in the operation unit 410, the manipulation unit 430 may detect the error and determine that the error has occurred. In addition, the manipulation unit 430 may record error information about the operation unit 410 by writing the error information to the operation unit 410. For example, details of the error that occurred in the operation unit 410, the position of at least one member included in the operation unit 410 where the error occurred, a current value input to at least one motor included in the surgical instrument, and the like may be written to the operation unit 410. The error information written to the operation unit 410 may be read by the control of the manipulation unit 430 or read by the control of another manipulation unit.

In addition, the manipulation unit 430 may transmit and receive information about the connector 420 based on the connection status of the first connection member 421. For example, the manipulation unit 430 may write or read information about the connector 420 (e.g., whether the connector 420 is in use, the number of times the connector 420 has been used, and the like) based on the state in which the first connection member 421 and the third contact 431 are connected to each other.

Meanwhile, the operation unit 410 and the manipulation unit 430 may each include a memory. The memory may include any non-transitory computer-readable recording medium. In an example, the memory may include a permanent mass storage device such as a RAM, a ROM, a disk drive, an SSD, a flash memory, or the like. In another example, the permanent mass storage device such as a ROM, an SSD, a flash memory, a disk drive, or the like may be a separate permanent storage device which is distinguishable from the memory. As another example, the memory may be a non-volatile storage device, such as an electrically erasable programmable read-only memory (EEPROM), that retains data for a long period even when the power supply is disconnected. In addition, the memory may store an operating system (OS) and at least one program code.

Figure 5:
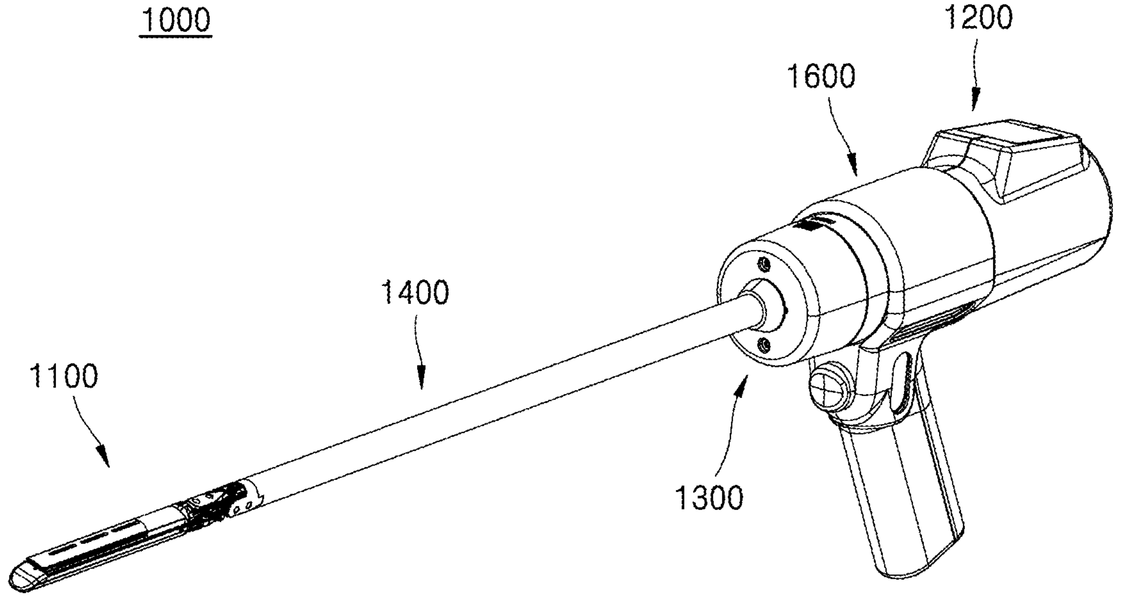
FIG. 5 is a perspective view illustrating a surgical instrument according to an embodiment.
Figure 6:
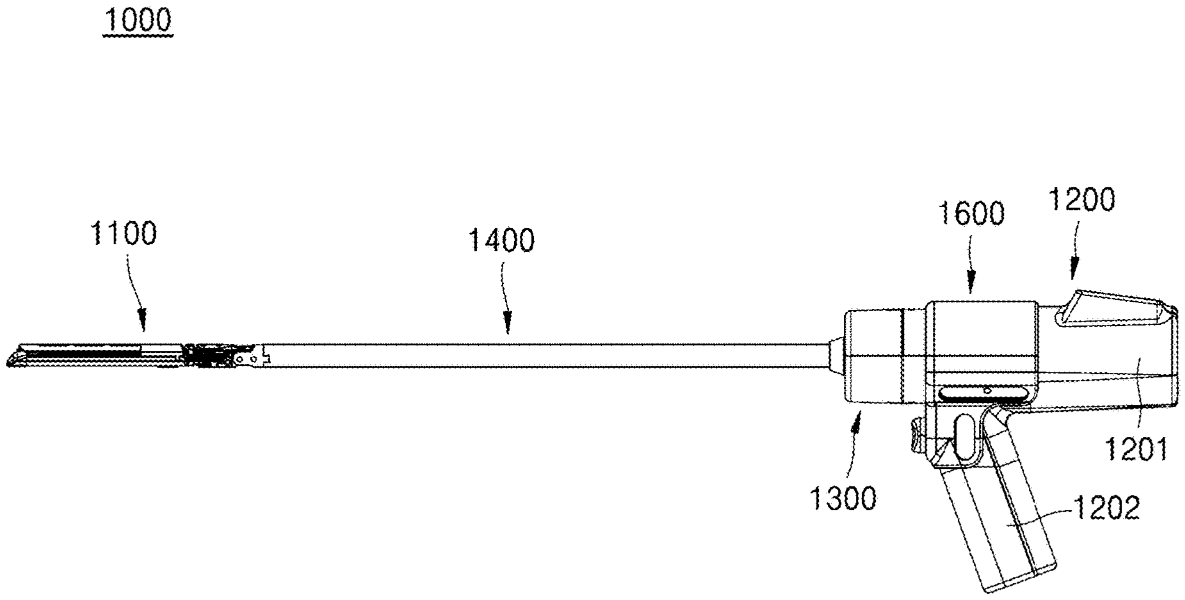
FIG. 6 is a side view of the surgical instrument of FIG. 5.

FIG. 5 is a perspective view illustrating a surgical instrument according to an embodiment, and FIG. 6 is a side view of the surgical instrument of FIG. 5.

Referring to FIGS. 5 and 6, a surgical instrument 1000 according to an embodiment of the present disclosure may include an end tool 1100, a manipulation unit 1200, a power transmission unit 1300, a connection unit 1400, and a connector 1600. For example, the end tool 1100, the power transmission unit 1300, and the connection unit 1400 may be included in an operation unit. Alternatively, the end tool 1100 and the connection unit 1400 may be included in the operation unit. However, examples of the operation unit are not limited to those described above.

Figure 7:
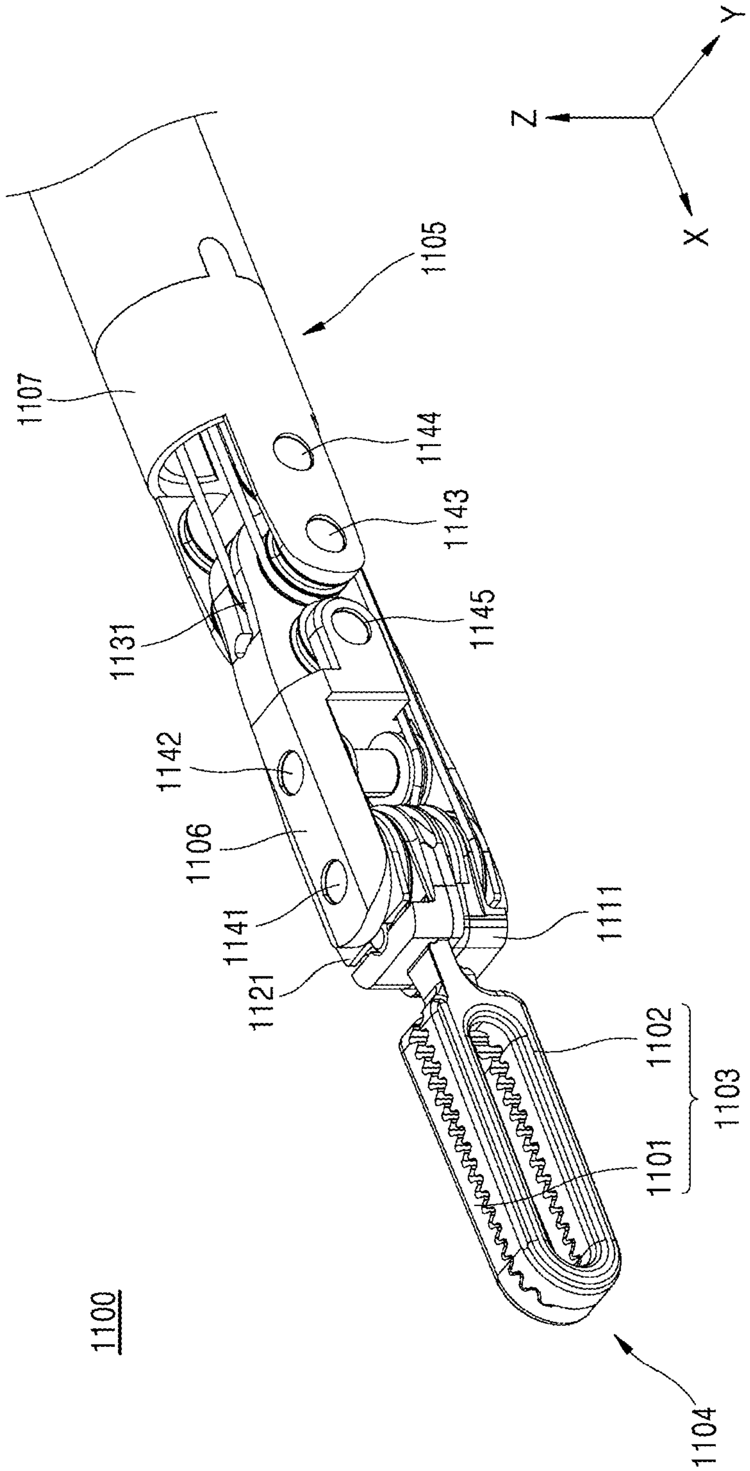
FIG. 7 is a perspective view illustrating an end tool according to an embodiment.

The end tool 1100 is formed on one end portion of the connection unit 1400, and performs necessary motions for surgery by being inserted into a surgical site. As an example of the end tool 1100 described above, a pair of jaws 1103 for performing a grip motion may be used as shown in FIG. 7 or the like. The above-described end tool 1100 is connected to the manipulation unit 1200 by the power transmission unit 1300 and the connection unit 1400, which will be described later, and receives a driving force of the manipulation unit 1200 through the power transmission unit 1300 and/or the connection unit 1400 to perform a motion necessary for surgery, such as gripping, cutting, suturing, or the like. However, the concept of the present disclosure is not limited thereto, and various devices for performing surgery may be used as the end tool 1100. For example, hereinafter, for convenience of description, the end tool 1100 used as a surgical clamp and an end tool 3100 used as a stapler are described by way of example, but the present disclosure is not limited thereto, and components such as a surgical grasper, a vessel sealer, and a one-armed cautery may also be used as the end tool.

A user may operate the end tool 1100 by manipulating the manipulation unit 1200. For example, the manipulation unit 1200 is a component for a user to input signals to control the motions of the end tool 1100. That is, the manipulation unit 1200 may be described as a component that receives signals from the user to control motions of the end tool 1100. Here, the signals for controlling the motions of the end tool 1100 may correspond to mechanical manipulations such as pressing a button or switch, or rotating or moving a particular member, and may also be electrical signals generated by such mechanical manipulations, but the present disclosure is not limited thereto. The manipulation unit 1200 is provided as an interface to be directly controlled by a medical doctor, for example, provided in a gun shape, a tongs shape, a stick shape, a lever shape, or the like, and when the medical doctor controls the manipulation unit 1200, the end tool 1100, which is connected to the corresponding interface and inserted into the body of a surgical patient, performs a certain motion, thereby performing surgery. Here, the manipulation unit 1200 is illustrated in FIG. 5 as being formed in a gun shape, but the concept of the present disclosure is not limited thereto, and various types of manipulation units that can be connected to the end tool 1100 and manipulate the end tool 1100 may be possible.

As an example, the manipulation unit 1200 may be a separate component or module separated from a drive module of the surgical instrument. Here, the drive module of the surgical instrument may refer to a part or module of the surgical instrument that includes the end tool 1100, and the power transmission unit 1300, the connection unit 1400, a power generation unit 1500, and the connector 1600 to be described later.

As a specific example, the drive module of the surgical instrument may be a separate component mountable to the manipulation unit 1200 that can be directly manipulated by the user. For example, the drive module of the surgical instrument may be detachably formed on the manipulation unit 1200. In this case, the drive module of the surgical instrument may include a module body, and the module body may include a coupling structure for coupling with the manipulation unit 1200.

As described above, when the drive module of the surgical instrument is detachably formed on the manipulation unit 1200, the user may easily replace the drive module of the surgical instrument as needed.

As another example, the manipulation unit 1200 may be replaced with a surgical robot. In other words, the drive module of the surgical instrument may be a separate component mountable to the surgical robot.

The surgical robot may refer to a robot that may perform surgery or other procedures by being manipulated by the user (e.g., a surgeon).

As a specific example, the surgical robot may include a master robot and a slave robot.

The master robot may include manipulation members that the user can grip and manipulate with both hands, and a display member that displays images captured through a laparoscope.

The slave robot may include one or more robot arm units. Here, each of the robot arm units may be provided in the form of a module that can operate independently of each other. Here, the drive module of the surgical instrument may be mounted to each of two or more of the robot arm units. For example, the drive module of the surgical instrument may be detachably formed on the surgical robot (specifically, on the slave robot). In this case, the drive module of the surgical instrument may include a module body, and the module body may include a coupling structure for coupling with the surgical robot.

As described above, when the drive module of the surgical instrument is detachably formed on the surgical robot, the user may easily replace the drive module of the surgical instrument as needed.

Hereinafter, for convenience of description, the technical idea of the present disclosure will be described in detail by taking the surgical instrument including the manipulation unit 1200 as an example. However, those skilled in the art will understand that the surgical instrument can also be implemented as the drive module of the surgical instrument formed to be mountable to the surgical robot or the manipulation unit that may be directly manipulated by a user.

The power transmission unit 1300 may be formed on another end portion of the connection unit 1400 and may serve to transmit power generated from the power generation unit to be described later to the end tool 1100. For example, the power transmission unit 1300 may be disposed between the end tool 1100 and the connector 1600. As will be described later, when a user such as a medical doctor manipulates the manipulation unit 1200, the power generation unit generates power to control the end tool 1100, and the generated power may be transmitted to the end tool 1100 through the power transmission unit 1300. The power transmission unit 1300 may include a plurality of wires, a plurality of pulleys, a plurality of links, a plurality of joints, a plurality of gears, and the like.

The connection unit 1400 is formed in the shape of a hollow shaft, in which one or more wires and electric wires may be accommodated. The connection unit 1400 has one end portion to which the manipulation unit 1200 is coupled and another end portion to which the power transmission unit is coupled, and the power transmission unit may be connected to the manipulation unit. In other words, it may be said that the connection unit 1400 may serve to connect the manipulation unit 1200 to the end tool 1100.

Meanwhile, a power connector (not shown) may be formed on the manipulation unit 1200. The power connector (not shown) may be connected to an external power source (not shown), and the power connector (not shown) may also be connected to the end tool 1100 via an electric wire, and may transmit, to the end tool 1100, electrical energy supplied from the external power source (not shown). In addition, the electrical energy, which is transmitted to the end tool 1100 as described above, may provide a driving force for performing a yaw rotation motion, a pitch rotation motion, an actuation motion, a staple motion, and the like of the end tool 1100 to be described later. Alternatively, the electrical energy transmitted to the end tool 1100 may provide a driving force for performing cutting and cauterizing functions of the end tool 1100, using a monopolar/bipolar or ultrasonic blade. In addition, the electrical energy may also be supplied to drive the power transmission unit 1300. Of course, a built-in battery may be used.

The manipulation unit 1200 may include a housing 1201 forming an outer shape of the manipulation unit 1200. As will be described later, at least a portion of the power generation unit configured to generate power to control the end tool 1100 may be accommodated inside the housing 1201. In addition, a circuit unit for controlling the operation of the power generation unit and a slip ring for supplying electrical energy to the power generation unit, connecting communication, or transmitting various other signals may be accommodated inside the housing 1201.

A handle 1202 may be formed on the manipulation unit 1200. The handle 1202 is a part for a user to grip. Thus, the user can use the surgical instrument 1000 according to the present disclosure while gripping the handle 1202 of the manipulation unit 1200.

Meanwhile, although not shown in the drawings, a button, a switch, a lever, and the like for controlling various motions of the end tool 1100 may be further formed in the manipulation unit.

Hereinafter, the end tool, the manipulation unit, the power transmission unit, the power generation unit, and the like of the surgical instrument of FIGS. 5 and 6 will be described in more detail.

Figure 8:
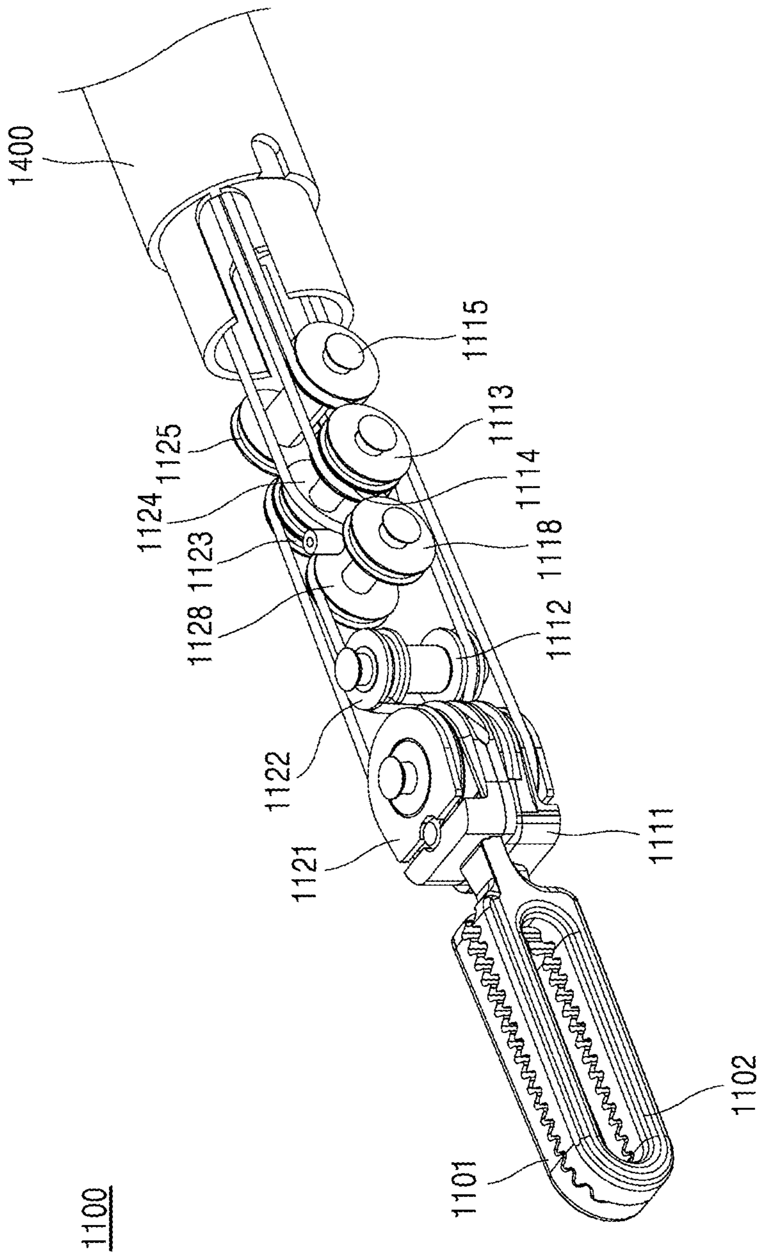
FIG. 8 is a perspective view illustrating the end tool of FIG. 7 with an end tool hub and a pitch hub removed.

FIG. 7 is a perspective view illustrating the end tool according to an embodiment, and FIG. 8 is a perspective view illustrating the end tool of FIG. 7 with an end tool hub and a pitch hub removed.

Referring to FIGS. 7 and 8, the end tool of the surgical instrument may include a first jaw 1101 and a second jaw 1102, each of which is formed to be rotatable.

In other words, the end tool 1100 of the surgical instrument according to an embodiment of the present disclosure may include a pair of jaws for performing a grip motion, that is, the first jaw 1101 and the second jaw 1102. Here, each of the first jaw 1101 and the second jaw 1102, or a component encompassing the first jaw 1101 and the second jaw 1102 may be referred to as the jaw 1103.

Here, the end tool 1100 of the surgical instrument 1000 according to an embodiment of the present disclosure is formed to be rotatable in at least one direction, for example, the end tool 1100 may perform a pitch motion around a Y-axis of FIG. 7 and simultaneously perform a yaw motion and an actuation motion around a Z-axis of FIG. 7.

Here, each of the pitch, yaw, and actuation motions used in the present disclosure are defined as follows.

First, the pitch motion means a motion of the end tool 1100 rotating in a vertical direction with respect to an extension direction of the connection unit 1400 (an X-axis direction of FIG. 7), that is, a motion rotating around the Y-axis of FIG. 7. In other words, the pitch motion means a motion of the end tool 1100, which is formed to extend from the connection unit 1400 in the extension direction of the connection unit 1400 (the X-axis direction of FIG. 7), rotating vertically around the Y-axis with respect to the connection unit 1400.

Next, the yaw motion means a motion of the end tool 1100 rotating in left and right directions, that is, a motion rotating around the Z-axis of FIG. 7, with respect to the extension direction of the connection unit 1400 the X-axis direction of FIG. 7. In other words, the yaw motion means a motion of the end tool 1100, which is formed to extend from the connection unit 1400 in the extension direction of the connection unit 1400 the X-axis direction of FIG. 7, rotating horizontally around the Z-axis with respect to the connection unit 1400. That is, the yaw motion means a motion of the two jaws 1103, which are formed on the end tool 1100, rotating around the Z-axis in the same direction.

Meanwhile, the actuation motion may mean a motion of the end tool 1100 rotating around the same axis of rotation as that of the yaw motion, while the two jaws 1103 rotate in the opposite directions so as to be closed or opened. That is, the actuation motion means a rotating motion of the two jaws 1103, which are formed on the end tool 1100, in the opposite directions around the Z-axis.

The end tool 1100 may include a plurality of pulleys including a pulley 1111 related to a rotational motion of the first jaw 1101. In addition, the end tool 1100 may include a plurality of pulleys, including a pulley 1121 associated with rotational movement of the second jaw 1102.

Here, the pulleys facing each other are illustrated in the drawings as being formed parallel to each other, but the concept of the present disclosure is not limited thereto, and each of the pulleys may be variously formed with a position and a size suitable for the configuration of the end tool.

Further, the end tool 1100 of the present embodiment may include an end tool hub 1106 and a pitch hub 1107.

A rotation shaft 1141 and a rotation shaft 1142 may be inserted through the end tool hub 1106, and the end tool hub 1106 may internally accommodate at least some of one or more pulleys that are axially coupled to the rotation shaft 1141. In addition, the end tool hub 1106 may internally accommodate at least some of one or more pulleys that are axially coupled to the rotation shaft 1142.

Meanwhile, a pulley 1131 serving as an end tool pitch pulley may be formed at one end portion of the end tool hub 1106. Alternatively, the pulley 1131 may be integrally formed with the end tool hub 1106 as one body. That is, a disk-shaped pulley is formed at one end portion of the end tool hub 1106, and a groove around which a wire may be wound may be formed on an outer circumferential surface of the pulley. Alternatively, the pulley 1131 may be formed as a separate member from the end tool hub 1106 to be coupled to the end tool hub 1106.

A rotation shaft 1143 and a rotation shaft 1144 are inserted through the pitch hub 1107, and the pitch hub 1107 may be axially coupled to the end tool hub 1106 and the pulley 1131 by the rotation shaft 1143. Thus, the end tool hub 1106 and the pulley 1131 may be formed to be rotatable around the rotation shaft 1143 with respect to the pitch hub 1107.

In addition, the pitch hub 1107 may internally accommodate at least some of one or more pulleys that are axially coupled to the rotation shaft 1143. In addition, the pitch hub 1107 may internally accommodate at least some of one or more pulleys that are axially coupled to the rotation shaft 1144.

In addition, the end tool 1100 of the present embodiment may include the rotation shaft 1141, the rotation shaft 1142, the rotation shaft 1143, and the rotation shaft 1144. As described above, the rotation shaft 1141 and the rotation shaft 1142 may be inserted through the end tool hub 1106, and the rotation shaft 1143 and the rotation shaft 1144 may be inserted through the pitch hub 1107. Further, in an optional embodiment, the end tool 1100 may further include a rotation shaft 1145.

The rotation shaft 1141, the rotation shaft 1142, the rotation shaft 1143, the rotation shaft 1144, and the rotation shaft 1145 may be arranged sequentially from a distal end 1104 of the end tool 1100 toward a proximal end 1105. Accordingly, starting from the distal end 1104, the rotation shaft 1141 may be referred to as a first pin, the rotation shaft 1142 may be referred to as a second pin, the rotation shaft 1145 may be referred to as a 2.5th pin, the rotation shaft 1143 may be referred to as a third pin, and the rotation shaft 1144 may be referred to as a fourth pin.

Here, the rotation shaft 1141 may function as an end tool jaw pulley rotation shaft, the rotation shaft 1142 may function as an end tool jaw auxiliary pulley rotation shaft, the rotation shaft 1143 may function as an end tool pitch rotation shaft, and the rotation shaft 1144 may function as an end tool pitch auxiliary rotation shaft of the end tool 1100. In addition, the rotation shaft 1145 may function as a pitch redundant rotation shaft of the end tool 1100.

One or more pulleys may be inserted into each of the rotation shafts 1141 1142, 1143, and 1144.

The pulley 1111 functions as an end tool first jaw pulley, and the pulley 1121 functions as an end tool second jaw pulley. The pulley 1111 may also be referred to as a first jaw pulley, and the pulley 1121 may be referred to as a second jaw pulley, and these two components may also be referred to collectively as an end tool jaw pulley or simply a jaw pulley.

The pulley 1111 and the pulley 1121, which are end tool jaw pulleys, are formed to face each other, and are formed to be rotatable independently of each other around the rotation shaft 1141, which is an end tool jaw pulley rotation shaft.

Here, in the drawings, it is illustrated that the pulley 1111 and the pulley 1121 are formed to rotate around one rotation shaft 1141, but it is of course possible that each end tool jaw pulley may be formed to be rotatable around a separate shaft. Here, the first jaw 1101 is fixedly coupled to the pulley 1111 and rotates together with the pulley 1111, and the second jaw 1102 is fixedly coupled to the pulley 1121 and rotates together with the pulley 1121. Yaw rotation and actuation motions of the end tool 1100 are performed in response to the rotation of the pulley 1111 and the pulley 1121. That is, when the pulley 1111 and the pulley 1121 are rotated in the same direction around the rotation shaft 1141, the yaw rotation motion is performed, and when the pulley 1111 and the pulley 1121 are rotated in opposite directions around the rotation shaft 1141, the actuation motion is performed.

Here, the first jaw 1101 and the pulley 1111 may be formed as separate members and coupled to each other, or the first jaw 1101 and the pulley 1111 may be integrally formed as one body. Similarly, the second jaw 1102 and the pulley 1121 may be formed as separate members and coupled to each other, or the second jaw 1102 and the pulley 1121 may be integrally formed as one body.

In addition, one or more auxiliary pulleys may be disposed adjacent to the pulley 1111 and the pulley 1112.

These pulleys may be formed such that one or more wires are wound therearound, the pulleys may be rotated by the wires, and the wires may move along the pulleys, thereby transmitting a driving force to the end tool 1100.

Meanwhile, the end tool 1100 described above is one example of the end tool that may be mounted to the surgical instrument 1000 according to the present disclosure, and the technical concept of the present disclosure is not limited thereto and some components may be changed, omitted or added as needed.

Figure 9:
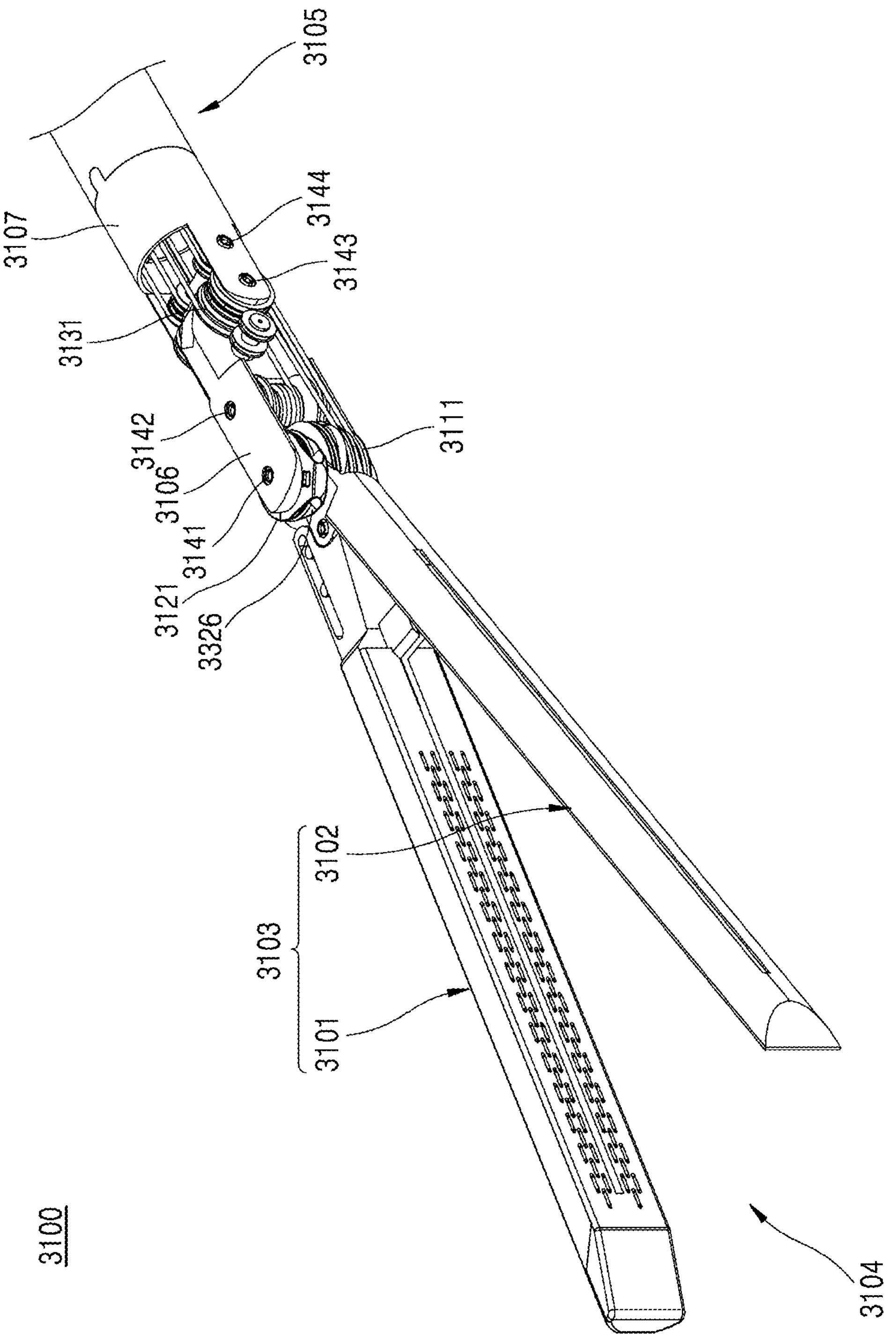
FIG. 9 is a perspective view illustrating an end tool according to another embodiment.
Figure 10:
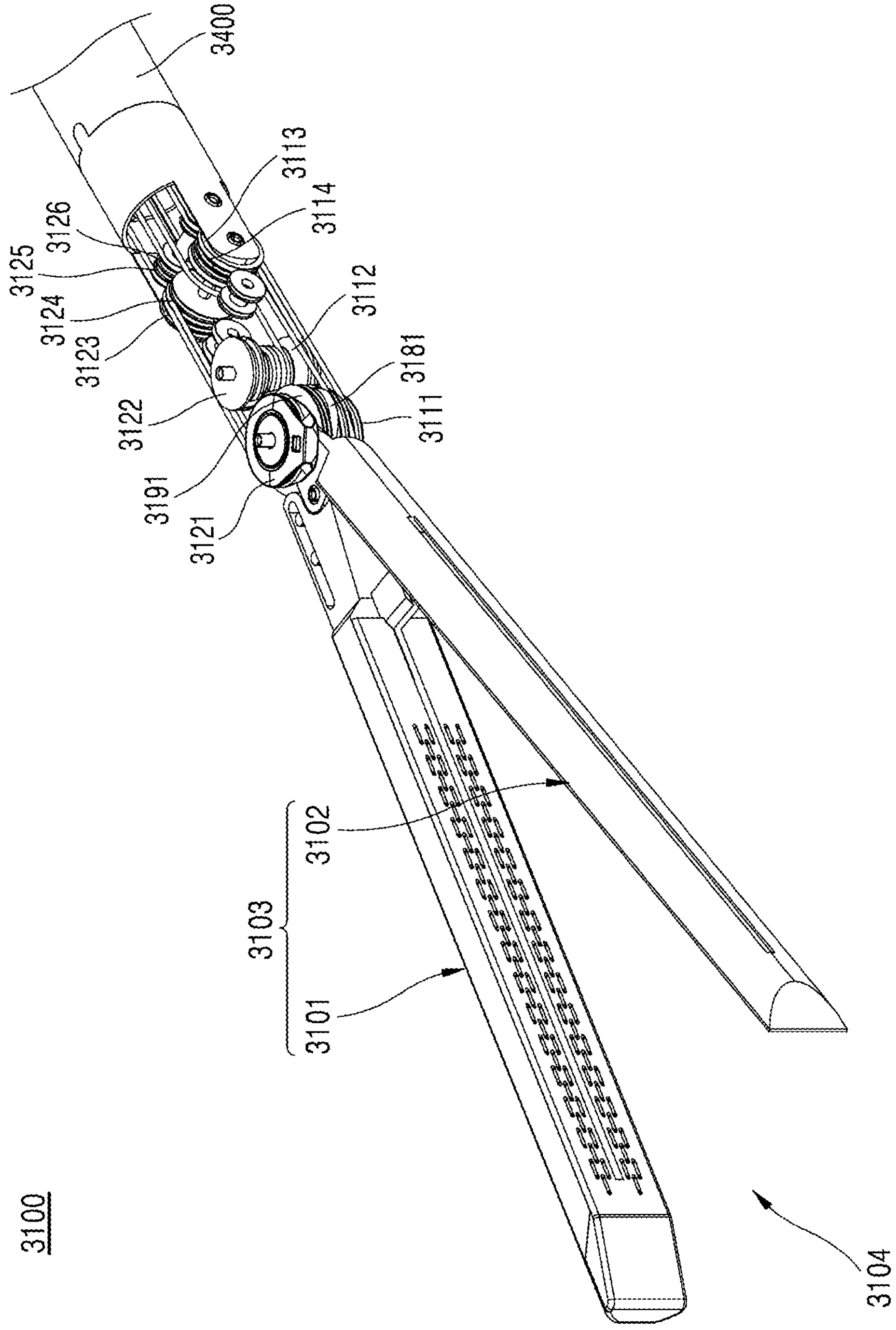
FIG. 10 is a perspective view illustrating the end tool of FIG. 9 with an end tool hub and a pitch hub removed.

FIG. 9 is a perspective view illustrating an end tool according to another embodiment, and FIG. 10 is a perspective view illustrating the end tool of FIG. 9 with an end tool hub and a pitch hub removed.

In other words, an end tool 3100 of the surgical instrument according to an embodiment of the present disclosure may include a pair of jaws for performing a grip motion, that is, a first jaw 3101 and a second jaw 3102. Here, each of the first jaw 3101 and the second jaw 3102, or a component encompassing the first jaw 3101 and the second jaw 3102 may be referred to as a jaw 3103.

Here, the end tool 3100 of a surgical instrument 3000 according to an embodiment of the present disclosure is formed to be rotatable in at least one direction, for example, the end tool 3100 may perform a pitch motion around the Y-axis (refer to FIG. 7) and simultaneously perform a yaw motion and an actuation motion around the Z-axis (refer to FIG. 7).

In addition, the end tool 3100 may include a plurality of pulleys including a pulley 3111 related to a rotational motion of the first jaw 3101. In addition, the end tool 3100 may include a plurality of pulleys, including a pulley 3121 associated with rotational movement of the second jaw 3102.

Here, the pulleys facing each other are illustrated in the drawings as being formed parallel to each other, but the concept of the present disclosure is not limited thereto, and each of the pulleys may be variously formed with a position and a size suitable for the configuration of the end tool.

Further, the end tool 3100 of the present embodiment may include an end tool hub 3106 and a pitch hub 3107.

A rotation shaft 3141 and a rotation shaft 3142 may be inserted through the end tool hub 3106, and the end tool hub 3106 may internally accommodate at least some of one or more pulleys that are axially coupled to the rotation shaft 3141. In addition, the end tool hub 3106 may internally accommodate at least some of one or more pulleys that are axially coupled to the rotation shaft 3142.

Meanwhile, a pulley 3131 serving as an end tool pitch pulley may be formed at one end portion of the end tool hub 3106. The pulley 3131 may be integrally formed with the end tool hub 3106 as one body. That is, a disk-shaped pulley is formed at one end portion of the end tool hub 3106, and a groove around which a wire may be wound may be formed on an outer circumferential surface of the pulley. Alternatively, the pulley 3131 may be formed as a separate member from the end tool hub 3106 to be coupled to the end tool hub 3106.

A rotation shaft 3143 and a rotation shaft 3144 are inserted through the pitch hub 3107, and the pitch hub 3107 may be axially coupled to the end tool hub 3106 and the pulley 3131 by the rotation shaft 3143. Thus, the end tool hub 3106 and the pulley 3131 may be formed to be rotatable around the rotation shaft 3143 with respect to the pitch hub 3107.

In addition, the pitch hub 3107 may internally accommodate at least some of one or more pulleys that are axially coupled to the rotation shaft 3143. In addition, the pitch hub 3107 may internally accommodate at least some of one or more pulleys that are axially coupled to the rotation shaft 3144.

In addition, the end tool 3100 of the present embodiment may include the rotation shaft 3141, the rotation shaft 3142, the rotation shaft 3143, and the rotation shaft 3144. As described above, the rotation shaft 3141 and the rotation shaft 3142 may be inserted through the end tool hub 3106, and the rotation shaft 3143 and the rotation shaft 3144 may be inserted through the pitch hub 3107.

The rotation shaft 3141, the rotation shaft 3142, the rotation shaft 3143, and the rotation shaft 3144 may be arranged sequentially from a distal end 3104 of the end tool 3100 toward a proximal end 3105. Accordingly, starting from the distal end 3104, the rotation shaft 3141 may be referred to as a first pin, the rotation shaft 3142 may be referred to as a second pin, the rotation shaft 3143 may be referred to as a third pin, and the rotation shaft 3144 may be referred to as a fourth pin.

Here, the rotation shaft 3141 may function as an end tool jaw pulley rotation shaft, the rotation shaft 3142 may function as an end tool jaw auxiliary pulley rotation shaft, the rotation shaft 3143 may function as an end tool pitch rotation shaft, and the rotation shaft 3144 may function as an end tool pitch auxiliary rotation shaft of the end tool 3100.

One or more pulleys may be inserted into each of the rotation shafts 3141, 3142, 3143, and 3144.

The pulley 3111 functions as an end tool first jaw pulley, and the pulley 3121 functions as an end tool second jaw pulley. The pulley 3111 may also be referred to as a first jaw pulley, and the pulley 3121 may also be referred to as a second jaw pulley, and these two components may also be referred to collectively as an end tool jaw pulley or simply a jaw pulley.

The pulley 3111 and the pulley 3121, which are end tool jaw pulleys, are formed to face each other, and are formed to be rotatable independently of each other around the rotation shaft 3141, which is an end tool jaw pulley rotation shaft. In this case, the pulley 3111 and the pulley 3121 are formed to be spaced apart from each other by a certain extent, and the staple assembly accommodation unit may be formed therebetween. In addition, at least some of the staple pulley assembly and the staple link assembly for stapling motion, which will be described later, may be disposed inside the staple assembly accommodation unit.

Here, in the drawings, it is illustrated that the pulley 3111 and the pulley 3121 are formed to rotate around one rotation shaft 3141, but it is of course possible that each end tool jaw pulley may be formed to be rotatable around a separate shaft. Here, the first jaw 3101 is fixedly coupled to the pulley 3111 and rotated together with the pulley 3111, and the second jaw 3102 is fixedly coupled to the pulley 3121 and rotated together with the pulley 3121. Yaw rotation and actuation motions of the end tool 3100 are performed in response to the rotation of the pulley 3111 and the pulley 3121. That is, when the pulley 3111 and the pulley 3121 are rotated in the same direction around the rotation shaft 3141, the yaw rotation motion is performed, and when the pulley 3111 and the pulley 3121 are rotated in opposite directions around the rotation shaft 3141, the actuation motion is performed.

Here, the first jaw 3101 and the pulley 3111 may be formed as separate members and coupled to each other, or the first jaw 3101 and the pulley 3111 may be integrally formed as one body. Similarly, the second jaw 3102 and the pulley 3121 may be formed as separate members and coupled to each other, or the second jaw 3102 and the pulley 3121 may be integrally formed as one body.

In addition, one or more auxiliary pulleys may be disposed adjacent to the pulley 3111 and the pulley 3121.

These pulleys may be formed such that one or more wires are wound therearound, the pulleys may be rotated by the wires, and the wires may move along the pulleys, thereby transmitting a driving force to the end tool 3100.

Figure 11:
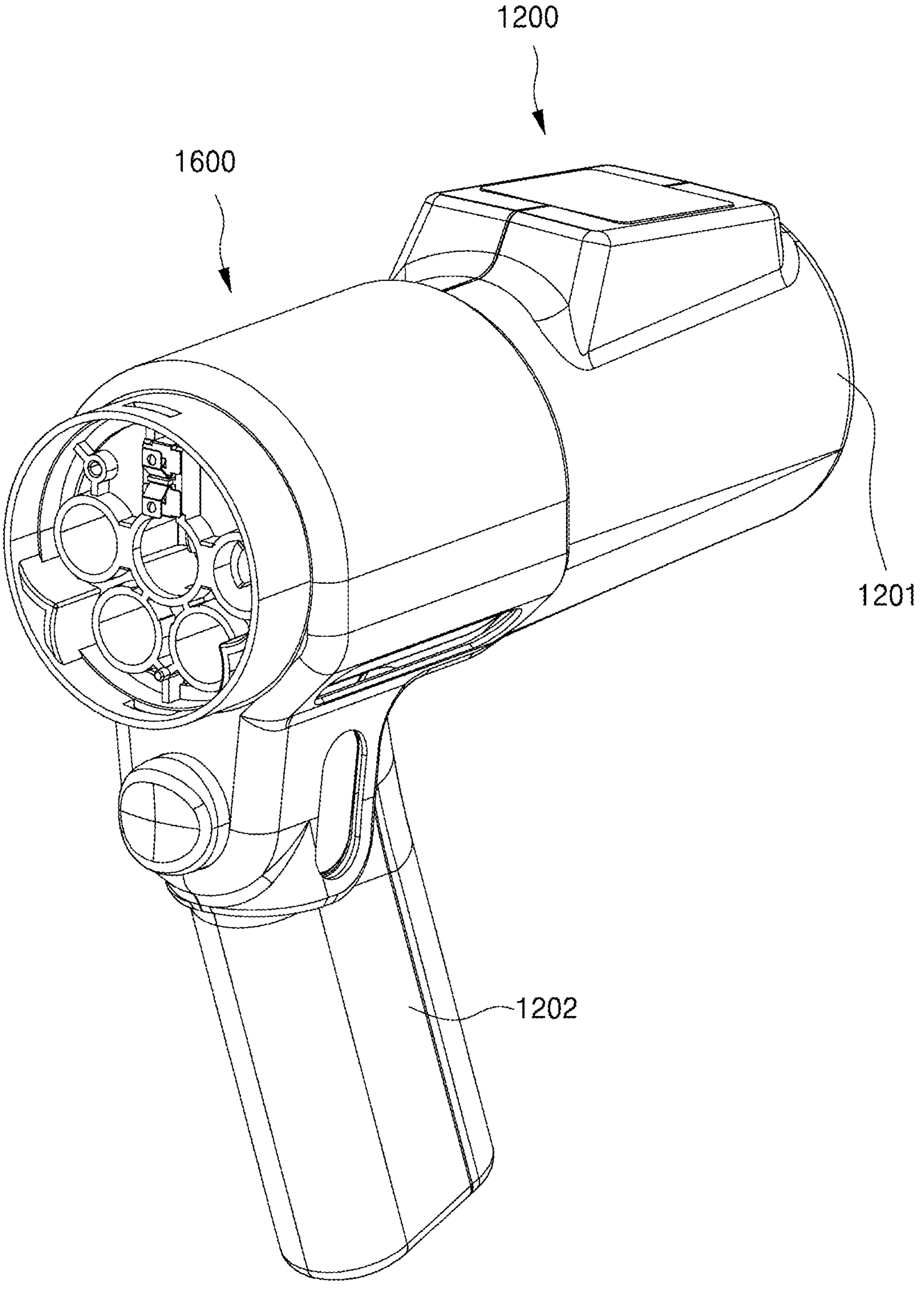
FIG. 11 is a view illustrating a connector and a manipulation unit according to an embodiment.
Figure 12:
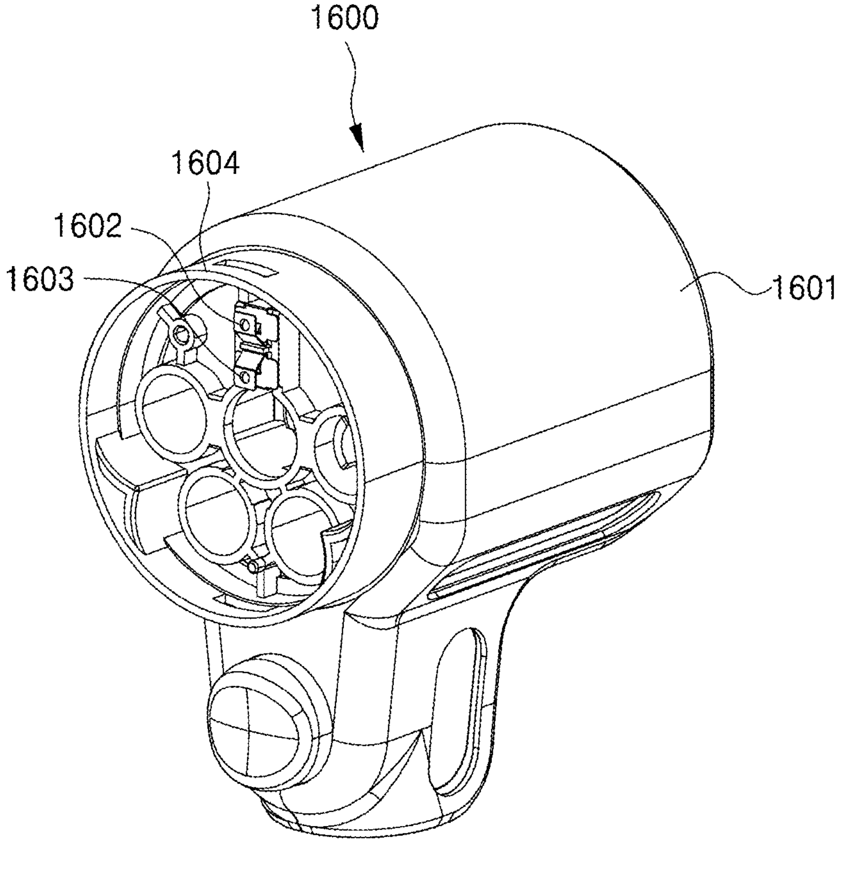
FIG. 12 is a view illustrating the connector according to an embodiment.
Figure 13:
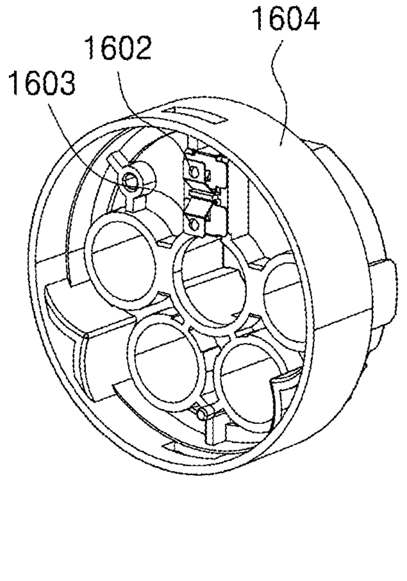
FIG. 13 is a view illustrating a connector base according to an embodiment.

FIG. 11 is a view illustrating a connector and the manipulation unit according to an embodiment, FIG. 12 is a view illustrating the connector according to an embodiment, and FIG. 13 is a view illustrating a connector base according to an embodiment.

The connector 1600 may be coupled to the manipulation unit 1200. For example, the connector 1600 may include a region that couples with a distal end of the manipulation unit 1200. In addition, the connector 1600 may be coupled to cover outer surfaces of mechanical components, such as buttons or switches, included in the manipulation unit 1200. However, the example of the connector 1600 is not limited those illustrated in FIG. 11.

Although not shown in the drawing, a drape included in the connector 1600 may cover an outer surface of the manipulation unit 1200 to protect the manipulation unit 1200 from contamination or the like. For example, as shown in FIG. 11, the connector 1600 may be coupled with a portion of the outer shape of the manipulation unit 1200, and the drape included in the connector 1600 may cover the housing 1201 and/or the handle 1202 to protect against contamination or the like. In addition, the connector 1600 may be coupled to the operation unit to cover an outer surface of the operation unit, thereby protecting the operation unit from contamination or the like.

Meanwhile, the connector 1600 may include a connector base 1604 and a connector plate 1601. By coupling the connector base 1604 and the connector plate 1601 with the power transmission unit 1300 and/or the manipulation unit 1200, the connector 1600 may be stably fixed between the power transmission unit 1300 and the manipulation unit 1200. For example, the power transmission unit 1300 may be coupled to one end portion of the connector base 1604, and the manipulation unit 1200 may be coupled to another end portion of the connector base 1604. Meanwhile, referring to FIGS. 11 and 12, the connector base 1604 and the connector plate 1601 are illustrated as separate components but may be a single component.

In addition, the connector 1600 may include a first connection member 1602 and a second connection member 1603. The first connection member 1602 and the second connection member 1603 may be coupled inside the connector base 1604. In other words, the connector base 1604 may accommodate the first connection member 1602 and the second connection member 1603 therein.

One end portion of the first connection member 1602 may be in contact with a first contact included in the operation unit, and another end portion thereof may be in contact with a third contact included in the manipulation unit 1200. For example, the first connection member 1602 may be connected to each of the first contact and the third contact to perform a communication operation.

One end portion of the second connection member 1603 may be in contact with a second contact included in the operation unit, and another end portion thereof may be in contact with a fourth contact and a fifth contact included in the manipulation unit 1200. For example, the second connection member 1603 may be connected to the second contact and/or the fourth contact to perform a ground operation. In addition, the second connection member 1603 may be connected to the fourth contact and the fifth contact to detect the mounting of the connector 1600.

Meanwhile, although not shown in the drawings, the connector 1600 may include a reuse prevention unit whose structure is deformed based on pressure generated as the connector is attached to or detached from the manipulation unit 1200. As an example, the reuse prevention unit may be a component that breaks and generates a sound signal while being mounted to the manipulation unit 1200. The generated sound signal is input to a circuit unit included in the manipulation unit 1200, and the circuit unit may compare the generated sound signal with a preset signal range. In addition, the manipulation unit 1200 may determine that the connector is normal when the generated sound signal falls within the preset signal range. Alternatively, when the generated sound signal does not fall within the preset signal range or no sound signal is generated, the manipulation unit 1200 may determine that the connector is reused or abnormal. As another example, the reuse prevention unit may be a structure that breaks when detached from the manipulation unit 1200, and subsequently deforms in a way that prevents the connector 1600 from being mounted on the manipulation unit 1200 or any other manipulation units.

Figure 14:
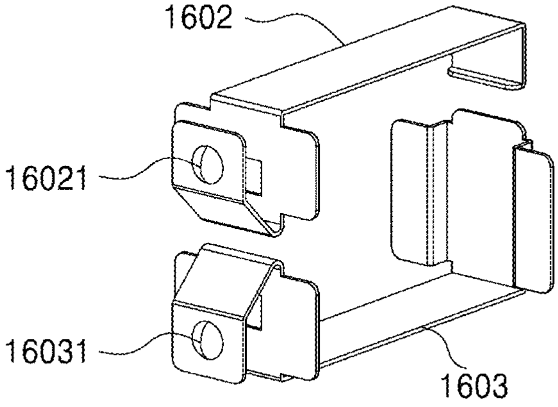
FIG. 14 is a view illustrating a first connection member and a second connection member according to an embodiment.
Figure 15:
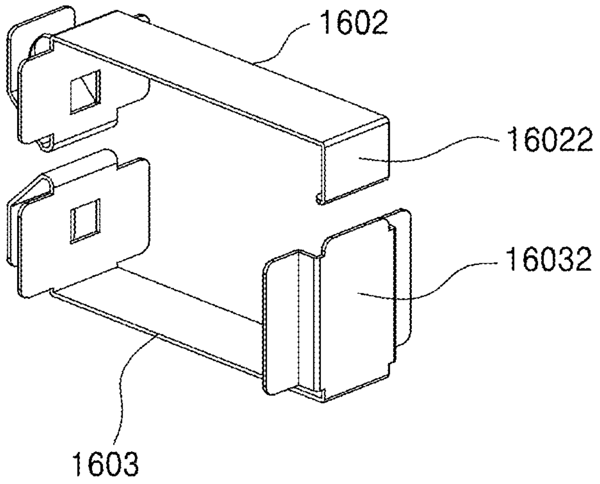
FIG. 15 is a view illustrating the first connection member and the second connection member of FIG. 14 as viewed from the rear side.

FIG. 14 is a view illustrating the first connection member and the second connection member according to an embodiment, and FIG. 15 is a view illustrating the first connection member and the second connection member of FIG. 14 as viewed from the rear side.

The first connection member 1602 may include a sixth contact 16021 and a seventh contact 16022. The sixth contact 16021 may be connected to the first contact included in the operation unit. The seventh contact 16022 may be connected to the third contact included in the manipulation unit 1200.

The second connection member 1603 may include an eighth contact 16031 and a ninth contact 16032. The eighth contact 16031 may be connected to the second contact included in the operation unit. The ninth contact 16032 may be connected to the fourth contact and/or the fifth contact included in the manipulation unit 1200.

In other words, the first connection member 1602 may be connected to the operation unit and the manipulation unit 1200 by means of the sixth contact 16021 and the seventh contact 16022. The first connection member 1602 may perform a communication operation of the surgical instrument by connecting the operation unit to the manipulation unit 1200 by means of the sixth contact 16021 and the seventh contact 16022.

In addition, the second connection member 1603 may be connected to the operation unit and the manipulation unit 1200 by means of the eighth contact 16031 and the ninth contact 16032. The second connection member 1603 may provide the ground of the surgical instrument to the operation unit and the manipulation unit 1200 by connecting the operation unit to the manipulation unit 1200 by means of the eighth contact 16031 and the ninth contact 16032. In addition, as the second connection member 1603 connects the operation unit to the manipulation unit 1200 by means of the eighth contact 16031 and the ninth contact 16032, the manipulation unit 1200 may detect the mounting of the operation unit. In addition, as the second connection member 1603 connects the connector 1600 and the manipulation unit 1200 by means of the ninth contact 16032, the manipulation unit 1200 may detect the mounting of the connector 1600.

Meanwhile, as shown in FIGS. 14 and 15, the first connection member 1602 and the second connection member 1603 may be leaf springs. In addition, as illustrated in FIGS. 14 and 15, the first connection member 1602 and the second connection member 1603 included in the connector are illustrated as separate plates, but may be integrally formed as one body. However, examples of the first connection member 1602 and the second connection member 1603 are not limited to those described above.

Figure 16:
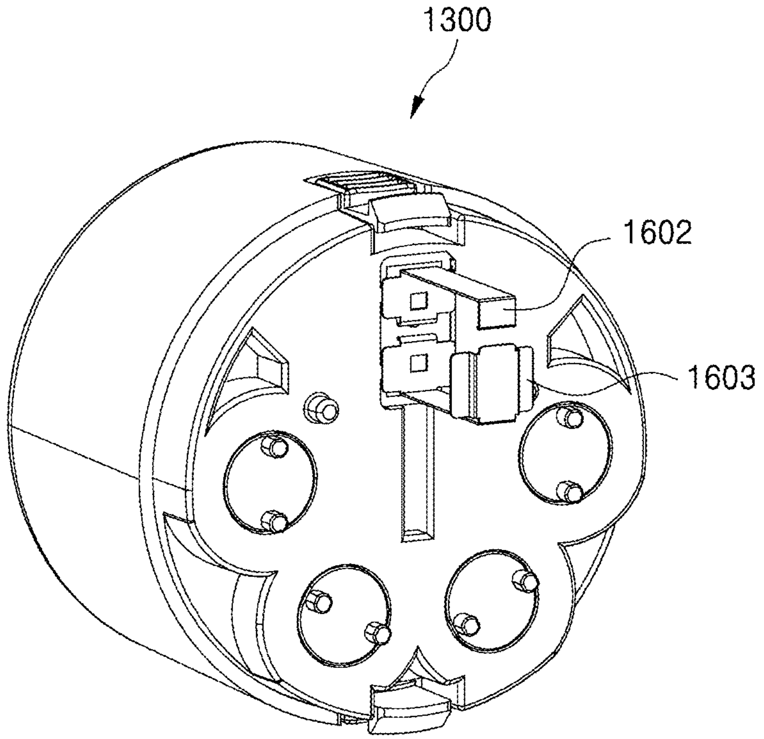
FIG. 16 is a view illustrating a power transmission unit, the first connection member, and the second connection member according to an embodiment.
Figure 17:
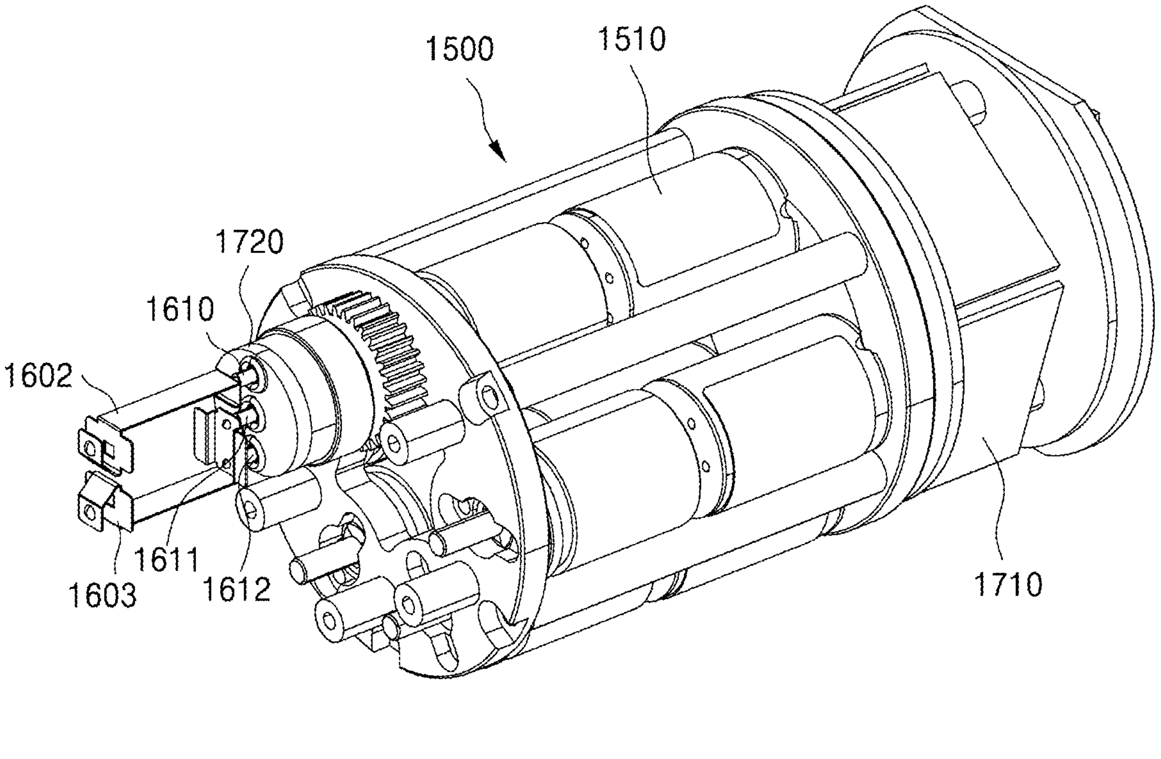
FIG. 17 is a view illustrating the power generation unit, the first connection member, and the second connection member according to an embodiment.

FIG. 16 is a view illustrating the power transmission unit, the first connection member, and the second connection member according to an embodiment, and FIG. 17 is a view illustrating the power generation unit, the first connection member, and the second connection member according to an embodiment.

The first connection member 1602 and the second connection member 1603 may be coupled to one end portion of the power transmission unit 1300. For example, the sixth contact included in the first connection member 1602 may be coupled to a first contact of the power transmission unit 1300. In addition, the eighth contact included in the second connection member 1603 may be coupled to a second contact of the power transmission unit 1300.

The first connection member and the second connection member may be coupled to one end portion of the power generation unit 1500. For example, the seventh contact included in the first connection member may be coupled to a third contact 1610 of the power generation unit 1500. In addition, the ninth contact included in the second connection member may be coupled to each of a fourth contact 1611 and a fifth contact 1612 of the power generation unit 1500.

Meanwhile, each of the third contact 1610, the fourth contact 1611, and the fifth contact 1612 may be an electrical connector. For example, each of the third contact 1610, the fourth contact 1611, and the fifth contact 1612 may include a pogo pin, a spring-loaded pin, or the like. However, examples of the third contact 1610, the fourth contact 1611, and the fifth contact 1612 are not limited to those described above.

Hereinafter, the power generation unit 1500 will be described in detail.

The power generation unit 1500 may be disposed to be at least partially accommodated in the housing (1201 of FIG. 6) of the manipulation unit (1200 of FIG. 6). Here, the housing (1201 of FIG. 6) may refer to a component that forms an outer shape of the manipulation unit (1200 of FIG. 6), but in the case of the drive module for the surgical instrument, the housing (1201 of FIG. 6) may refer to a component that forms an outer shape of the module body.

When a user manipulates the manipulation unit (1200 of FIG. 6), the power generation unit 1500 may generate power to control the end tool (1100 of FIG. 6) based on the manipulation.

The power generation unit 1500 may include a motor pack 1510 including at least one motor.

The motor pack 1510 may roll-rotate in a direction in which the connection unit (1400 of FIG. 6) extends.

Here, a roll motion as used herein is defined as follows.

The roll motion refers to a motion in which the end tool (1100 of FIG. 6), the connection unit (1400 of FIG. 6), the motor pack 1510, and the like, which constitute the surgical instrument (1000 of FIG. 6), rotate around an axis formed in a direction in which the connection unit (1400 of FIG. 6) extends. In other words, the roll motion refers to a motion of rotating around an axis formed in an extension direction (the X-axis direction of FIG. 7) of the connection unit (1400 of FIG. 6) without bending in a Y-axis direction of FIG. 7 or a Z-axis direction of FIG. 7.

At least a portion of the power generation unit 1500 may be accommodated inside the housing (1201 of FIG. 6) of the manipulation unit (1200 of FIG. 6). In this case, the motor pack 1510 is accommodated in the housing (1201 of FIG. 6) of the manipulation unit (1200 of FIG. 6). Here, the phrase "the motor pack 1510 roll-rotates" may mean that the motor pack 1510 rotates inside the housing (1201 of FIG. 6) along an inner circumferential surface of the housing (1201 of FIG. 6). In other words, when a user performs a manipulation to roll-rotate the manipulation unit (1200 of FIG. 6) while grasping a handle (1202 of FIG. 6) of the manipulation unit (1200 of FIG. 6), the motor pack 1510 may rotate around the axis, which is formed in the direction in which the connection unit (1400 of FIG. 6) extends, inside the housing (1201 of FIG. 6) while the housing (1201 of FIG. 6) and the handle (1202 of FIG. 6) of the manipulation unit (1200 of FIG. 6) are fixed in place. In other words, it may be said that the housing (1201 of FIG. 6) and the handle (1202 of FIG. 6) rotate when the user performs a manipulation for a roll motion while grasping the connection unit (1400 of FIG. 6).

The motor pack 1510 may include at least one motor. For example, the motor pack 1510 may include at least one motor that generates power to drive the end tool (1100 of FIG. 6) based on a signal input to the manipulation unit (1200 of FIG. 6).

The motor pack 1510 may include a yaw drive motor. The yaw drive motor may generate power to yaw-rotate the end tool (1100 of FIG. 6). For example, when a user manipulates the manipulation unit (1200 of FIG. 6) to yaw-rotate the end tool (1100 of FIG. 6), the yaw drive motor may generate a driving force to yaw-rotate the end tool (1100 of FIG. 6).

The motor pack 1510 may include a pitch drive motor. The pitch drive motor may generate power to pitch-rotate the end tool (1100 of FIG. 6). For example, the pitch drive motor may generate a driving force to pitch-rotate the end tool (1100 of FIG. 6) when a user manipulates the manipulation unit (1200 of FIG. 6) to pitch-rotate the end tool (1100 of FIG. 6).

The motor pack 1510 may include a roll drive motor that generates power to perform roll rotation. For example, the roll drive motor may generate a driving force to roll-rotate the motor pack 1510 when a user manipulates the manipulation unit (1200 of FIG. 6) to rotate the motor pack 1510.

For example, the roll drive motor may be included in the motor pack 1510. The roll drive motor may be provided together with the yaw drive motor and the pitch drive motor inside the motor pack 1510. The roll drive motor may be driven by the user's manipulation to generate driving force to rotate the motor pack 1510. In this case, the roll drive motor may move together with the motor pack 1510. For example, when the motor pack 1510 is rotated by the roll drive motor, the roll drive motor, as a component included in the motor pack 1510, may rotate together with the motor pack 1510.

As another example, the roll drive motor may not be provided in the motor pack 1510. For example, the roll drive motor may be disposed outside the motor pack 1510. The roll drive motor may be driven by the user's manipulation to generate driving force to rotate the motor pack 1510. In this case, the roll drive motor may move independently from the motor pack 1510. For example, the motor pack 1510 may be rotated by the roll drive motor, but the roll drive motor may not rotate together with the motor pack 1510, and specifically, the yaw drive motor, the pitch drive motor, and a firing drive motor may rotate together, but the roll drive motor may not rotate together.

Hereinafter, for convenience of description, the roll drive motor will be described as being included in the motor pack 1510 by way of example, but it will be understood by those skilled in the art that the roll drive motor may not be included in the motor pack 1510 in the following description. In addition, those skilled in the art will understand that, when the roll drive motor is not included in the motor pack 1510, the following content may be appropriately modified and applied.

The motor pack 1510 may include the firing drive motor. The firing drive motor may generate power to linearly move the operation member of the end tool (1100 of FIG. 6). For example, the firing drive motor may generate a driving force to linearly move the operation member when a user manipulates the manipulation unit (1200 of FIG. 6) to linearly move the operation member of the end tool (1100 of FIG. 6).

For example, the roll drive motor, the yaw drive motor, the pitch drive motor and the firing drive motor may be disposed side by side with each other. In addition, the roll drive motor, the yaw drive motor, the pitch drive motor and the firing drive motor may be disposed to form a circular pattern.

As described above, the motor pack 1510 may roll-rotate inside the housing (1201 of FIG. 6) of the manipulation unit (1200 of FIG. 6). In this case, since the motor pack 1510 includes a plurality of motors, by disposing the roll drive motor, the yaw drive motor, the pitch drive motor, and the firing drive motor to form a circular pattern with each other, when the motor pack 1510 rotates, a diameter of a space occupied by the rotation of the motor pack 1510 may be minimized. That is, by disposing the roll drive motor, the yaw drive motor, the pitch drive motor, and the firing drive motor to form a circular pattern, an inner diameter inside the housing (1201 of FIG. 6) necessary for the rotation of the motor pack 1510 may be designed to be small, which may contribute to miniaturization and lightweighting of the surgical instrument (1000 of FIG. 6).

Meanwhile, disposing the roll drive motor, the yaw drive motor, the pitch drive motor, and the firing drive motor to form a circular pattern does not mean that the roll drive motor, the yaw drive motor, the pitch drive motor, and the firing drive motor are disposed to be equally spaced from each other, but rather it is sufficient when outer circumferential surfaces of the roll drive motor, the yaw drive motor, the pitch drive motor, and the firing drive motor are disposed within a single circle.

For example, the roll drive motor, the yaw drive motor, the pitch drive motor, and the firing drive motor may be provided with different performance characteristics. For example, the magnitudes of driving forces that the roll drive motor, the yaw drive motor, the pitch drive motor, and the firing drive motor must generate to perform their respective roles may be different from each other. To this end, the roll drive motor, the yaw drive motor, the pitch drive motor, and the firing drive motor may have different outputs or sizes as necessary.

Meanwhile, a circuit unit may be disposed in the internal space of the manipulation unit 1200.

The circuit unit is a configuration including an electronic circuit for determining whether the operation unit and/or the connector is mounted, reading and/or writing information about the operation unit and/or the connector, or controlling the driving of the motor pack 1510. For example, the circuit unit may determine whether at least one of the connector and the operation unit (e.g., the end tool or the like) is mounted based on the connection status of the second connection member, or may write or read information about at least one of the connector and the operation unit based on the connection status of the first connection member. As an example, the circuit unit may include a motor driver, a motor controller, and a microcontroller unit, but the present disclosure is not limited thereto, and any component may be used as the circuit unit as long as it can drive the motor pack 1510.

The circuit unit may be implemented in an array of multiple logic gates, or in a combination of a universal microprocessor and a memory that stores a program executable in the microprocessor. For example, the circuit unit may include a general-purpose processor, a CPU, a microprocessor, a DSP, a controller, a microcontroller, a state machine, and the like. In some environments, the circuit unit may include an ASIC, a PLD, an FPGA, or the like. For example, the circuit unit may refer to a combination of processing devices such as, for example, a combination of a DSP and a microprocessor, a combination of a plurality of microprocessors, a combination of one or more microprocessors in conjunction with a DSP core, or a combination of any other such configuration.

The circuit unit may include a main board 1710 and a sub-board 1720.

The main board 1710 may be disposed at one end portion of the motor pack 1510. For example, the main board 1710 may be disposed at the rear of the motor pack 1510 based on FIG. 17 (i.e., in the opposite direction of the connection unit (1400 of FIG. 6)).

Although not shown in the drawings, in order to drive the motor pack 1510, the main board 1710 and the motor pack 1510 may be connected to each other through a plurality of electric wires. Thus, as the motor pack 1510 roll-rotates, the main board 1710 also rotates together with the motor pack 1510, so that a problem of twisting the plurality of electric wires connecting the motor pack 1510 to the main board 1710 can be prevented.

The sub-board 1720 may be disposed at another end portion of the motor pack 1510. For example, the sub-board 1720 may be disposed in the front of the motor pack 1510 based on FIG. 17 (i.e., in the direction of the connection unit (1400 of FIG. 6)).

The sub-board 1720 may assist the operation of the main board 1710. In addition, the sub-board 1720 may transmit a signal received from the operation unit or the connector to the main board 1710, or transmit a signal received from the main board 1710 to the operation unit or the connector.

In an embodiment, although not shown in the drawings, the surgical instrument may further include at least one sub-circuit unit. The sub-circuit unit may be disposed inside the manipulation unit (1200 of FIG. 6). In an exemplary embodiment, the sub-circuit unit may be disposed on a portion of the handle (1202 of FIG. 6) of the manipulation unit (1200 of FIG. 6). In this case, the sub-circuit unit may not rotate even when the motor pack 1510 rotates.

The sub-circuit unit may preprocess various signals for controlling the motor pack 1510. In addition, the sub-circuit unit may transmit the preprocessed signals to the circuit unit. To this end, the circuit unit may be connected to the sub-circuit unit by serial communication or the like, but the present disclosure is not limited thereto, and the circuit unit may be connected to the sub-circuit unit in various ways.

In an embodiment, although not shown in the drawings, the surgical instrument may further include a component for setting a zero point of roll rotation of the motor pack 1510 or the like. For example, the surgical instrument may further include at least one encoder for measuring a roll rotation angle of the motor pack 1510 or the like. Alternatively, the surgical instrument may further include a touch sensor, a Hall effect sensor, a photo sensor, or the like to measure the roll rotation angle of the motor pack 1510. However, the present disclosure is not limited thereto, and any component capable of measuring the roll rotation angle of the motor pack 1510 or the like may be provided in the surgical instrument of the present disclosure.

Figure 18:
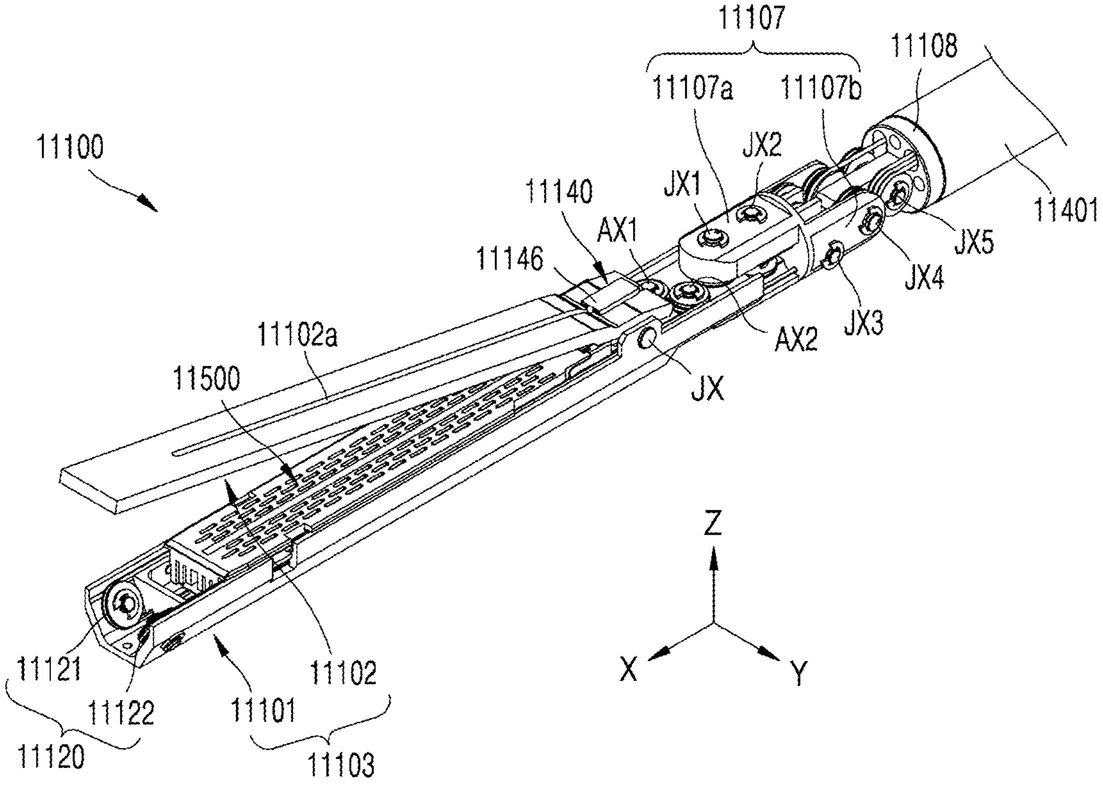
FIG. 18 is a schematic perspective view for describing an end tool according to another embodiment of the present disclosure.
Figure 19:
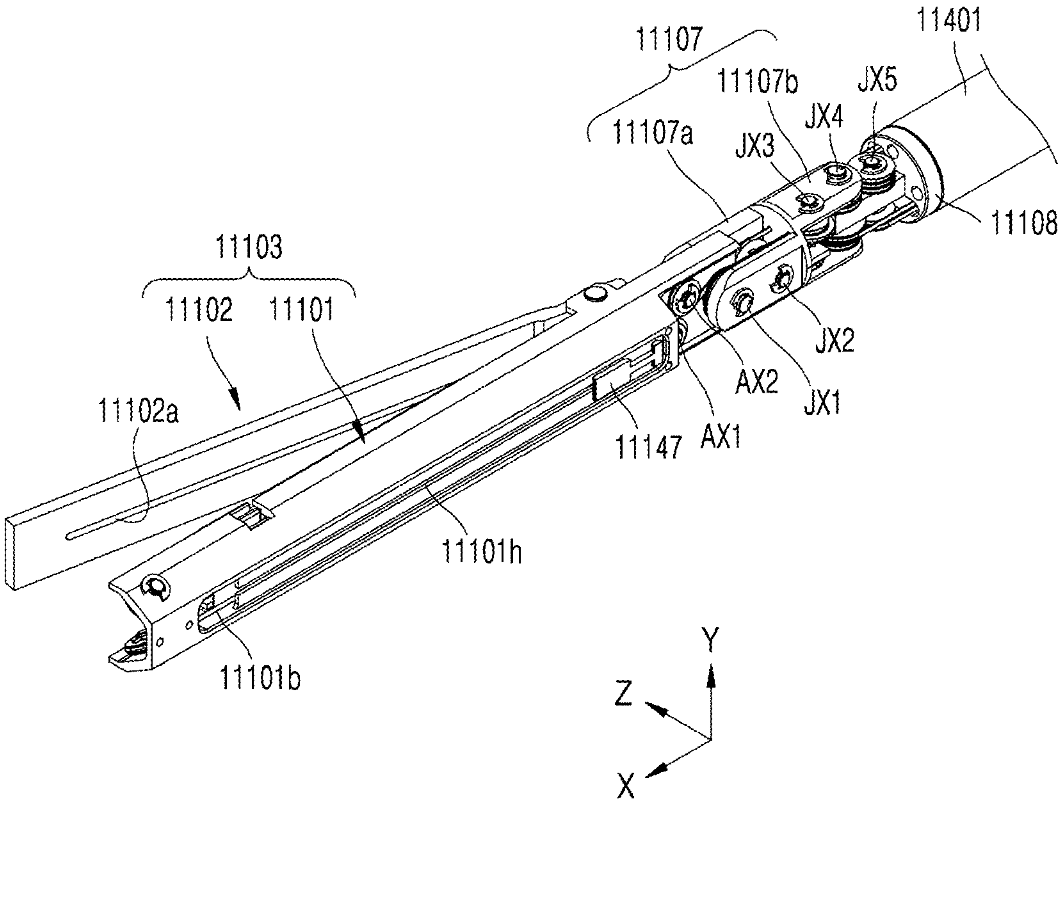
FIG. 19 is a perspective view of the end tool of FIG. 18 viewed from another direction.
Figure 20:
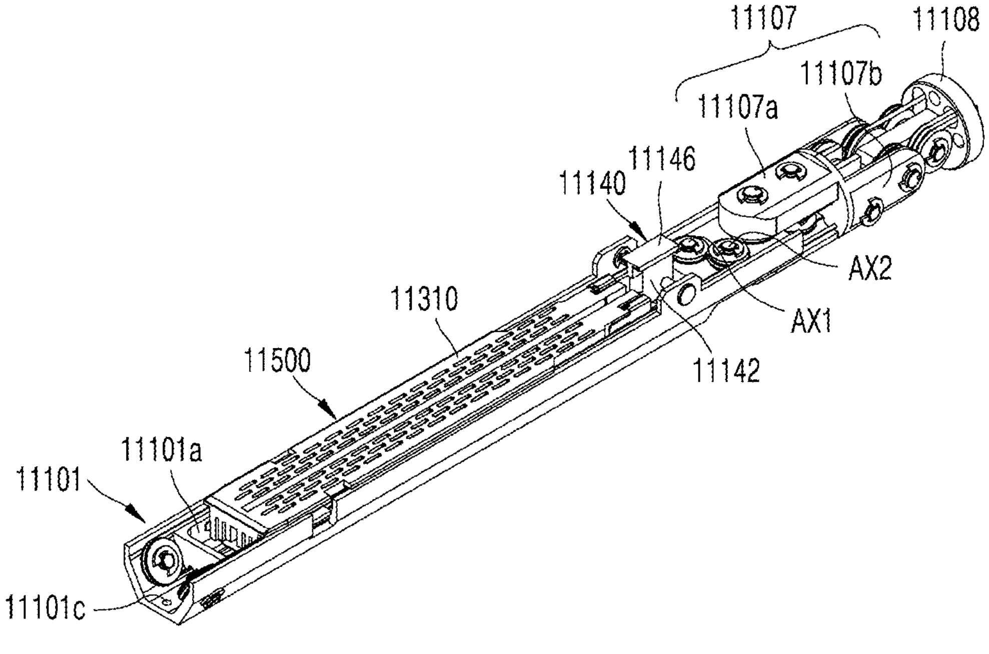
FIG. 20 is a schematic perspective view of the end tool of FIG. 18 with a second jaw removed.
Figure 21:
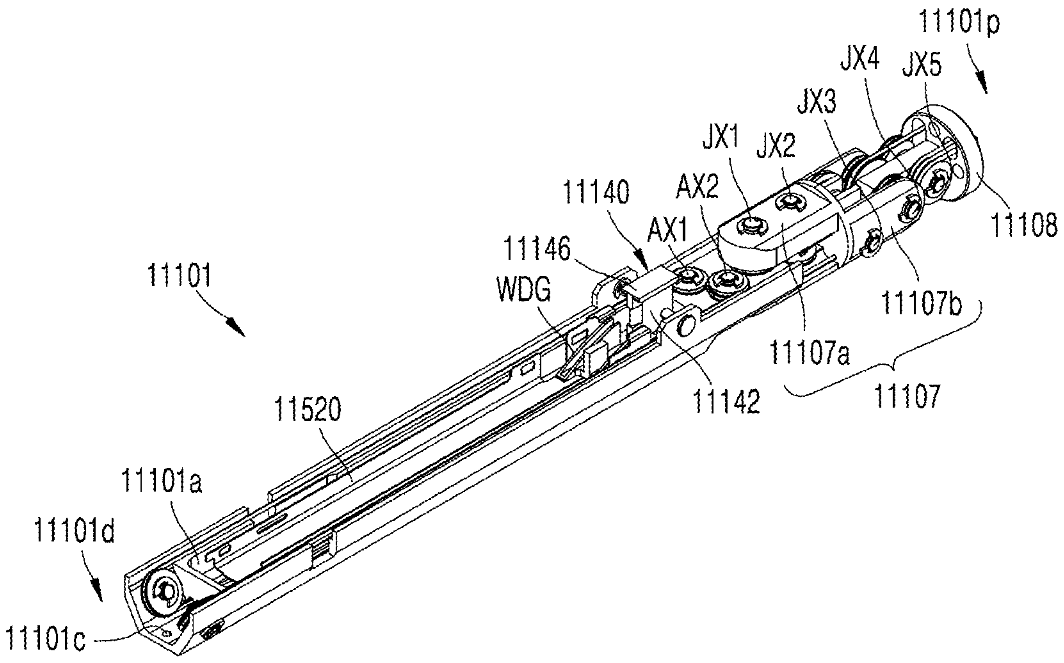
FIG. 21 is a schematic perspective view of the end tool of FIG. 20 with a cartridge removed.
Figure 22:
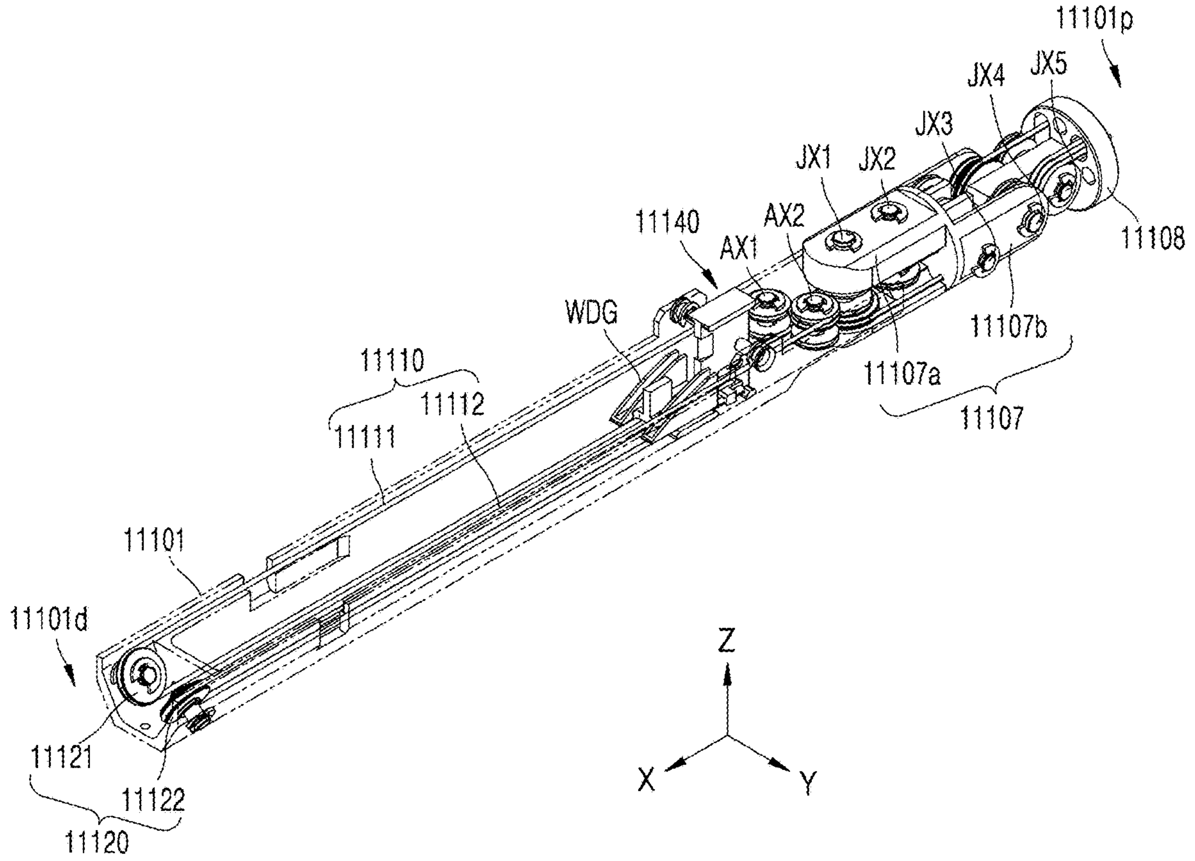
FIG. 22 is a transparent perspective view of FIG. 21.
Figure 23:
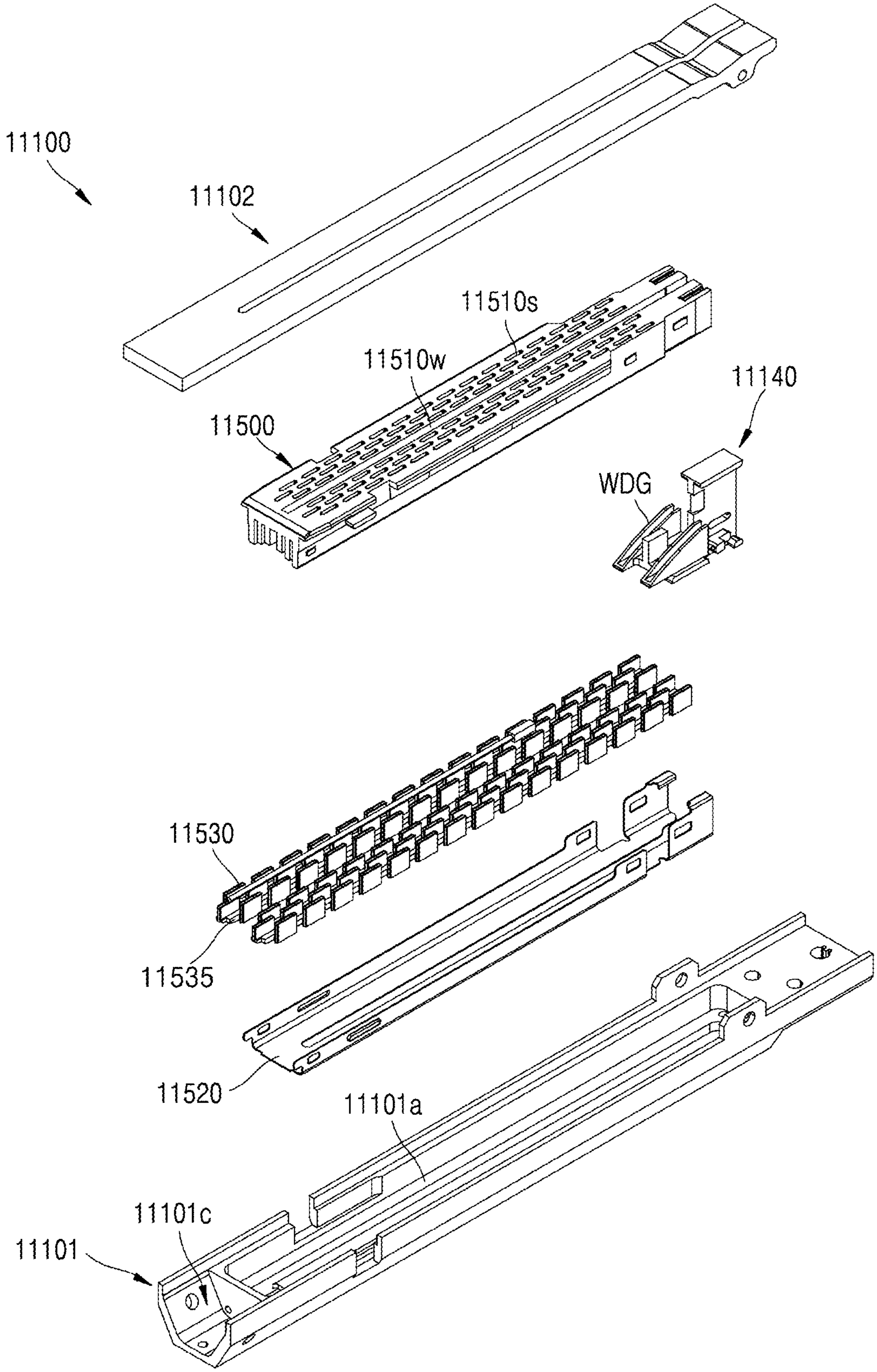
FIG. 23 is a perspective view illustrating a first jaw and the cartridge of the end tool of FIG. 18.

FIG. 18 is a schematic perspective view for describing an end tool according to another embodiment of the present disclosure, and FIG. 19 is a perspective view of the end tool of FIG. 18 viewed from another direction. FIG. 20 is a schematic perspective view of the end tool of FIG. 18 with a second jaw removed, FIG. 21 is a schematic perspective view of the end tool of FIG. 20 with a cartridge removed, and FIG. 22 is a transparent perspective view of FIG. 21. FIG. 23 is a perspective view illustrating a first jaw and the cartridge of the end tool of FIG. 18.

An end tool 11100 may include a jaw 11103, a plurality of fixed pulleys 11120, and a plurality of forward-moving wires 11110. The plurality of fixed pulleys 11120 may include two or more pulleys, for example, a first fixed pulley 11121 and a second fixed pulley 11122. The plurality of forward-moving wires 11110 include two or more wires, and may include, for example, a first forward-moving wire 11111 and a second forward-moving wire 11112.

The jaw 11103 may perform various functions, for example, a grip motion, and may include a pair of jaws, e.g., a first jaw 11101 and a second jaw 11102 as a specific example. Here, each of the first jaw 11101 and the second jaw 11102, or a component encompassing the first jaw 11101 and the second jaw 11102 may be referred to as the jaw 11103.

The first jaw 11101 and the second jaw 11102 may be disposed to face each other, may move closer to or move away from each other, and may be formed to rotationally move around, for example, one shaft JX.

A cartridge 11500 may be disposed to be accommodated in the first jaw 11101, and a plurality of staples are disposed inside the cartridge 11500. When an operation member 11140 receives a force through the plurality of forward-moving wires 11110 while the first jaw 11101 and the second jaw 11102 are close to each other, such as when the first jaw 11101 and the second jaw 11102 are closed with the body tissue interposed therebetween, the operation member 11140 may push and raise the staples while moving toward a distal end 11101*d* of the first jaw 11101, so that stapling may be performed. At this point, one or more clamps 11146 and 11147 of the operation member 11140 may protrude to the outside of the first jaw 11101 and the second jaw 11102, allowing the operation member 11140 to move forward while applying pressure to an outer surface of the first jaw 11101 and the second jaw 11102, which facilitates the smooth progression of a stapling process. In an optional embodiment, the cartridge 11500 may include a case 11520 corresponding to the bottom, and the case 11520 is disposed in the first jaw 11101.

Meanwhile, the operation member 11140 may be used together with a wedge WDG. For example, the wedge WDG may be prepared separately from the operation member 11140 and then disposed adjacent to the operation member 11140 in the first jaw 11101. In addition, as another example, the operation member 11140 and the wedge WDG may be integrally formed as one body. The wedge WDG may be disposed on at least one side of a body 11142 and may be formed to have a predetermined inclined surface. That is, the wedge WDG may be formed to be inclined by a certain degree with respect to an extension direction of the end tool 11100. In other words, the wedge WDG may be formed to have a greater height at a proximal end 11101*p* side of the first jaw 11101 than the distal end 11101*d* side of the first jaw 11101.

The wedge WDG may be formed to be sequentially in contact with withdrawal members 11535 or a plurality of staples 11530 disposed in the cartridge 11500, and may serve to sequentially push and raise the staples 11530.

The plurality of fixed pulleys 11120 may be disposed in the first jaw 11101 to be closer to the front of the cartridge 11500, i.e., to the distal end 11101*d* of the first jaw 11101, than the cartridge 11500. For example, the plurality of fixed pulleys 11120 may be disposed in a front space 11101*c* of the first jaw 11101, and details thereof will be described later.

In addition, the end tool 11100 of the surgical instrument of the present embodiment may include one or more members, such as joint members, that connect the jaw 11103 to a connection unit. Further, in an optional embodiment, the end tool 11100 may include an end tool hub 11108 and a pitch hub 11107.

The end tool hub 11108 may be disposed to connect the end tool 11100 to a straight unit 11401 of the connection unit.

As an example, the end tool hub 11108 may have a pulley shaft JX4 corresponding thereto, and the pulley shaft JX4 may be a pitch rotation shaft. As a specific example, the end tool 11100 may perform a vertical rotational motion around the pulley shaft JX4 based on the drawing. In addition, one or more pulleys may be disposed to be adjacent to the pulley shaft JX4.

The end tool hub 11108 may be in the form of a bar extending from the center of a surface thereof that corresponds to the connection unit, i.e., a bar extending from the center of a disk-shaped main region. The pulley shaft JX4 and a pulley shaft JX5 different from the pulley shaft JX4 may further correspond to a region of the bar.

The pitch hub 11107 is connected to the end tool hub 11108 and the jaw 11103. The pitch hub 11107 may be axially coupled to the end tool hub 11108 with respect to one pulley shaft, i.e., the pulley shaft JX4. The pitch hub 11107 may rotationally move around one pulley shaft, i.e., the pulley shaft JX4 while connected to the end tool hub 11108. That is, the end tool 11100 may perform a pitch motion as the pitch hub 11107 rotates around one pulley shaft, i.e., the pulley shaft JX4 with respect to the end tool hub 11108.

Further, the jaw 11103 of the end tool 11100 may be axially coupled to the pitch hub 11107 with respect to one pulley shaft, i.e., a pulley shaft JX1. The jaw 11103 may rotate around one pulley shaft, i.e., the pulley shaft JX1 while connected to the pitch hub 11107. That is, the jaw 11103 of the end tool 11100 may rotate around one pulley shaft, i.e., the pulley shaft JX1 with respect to the pitch hub 11107, thereby performing a yaw motion.

As a result, the yaw motion of the end tool 11100 includes a rotational motion of the jaw 11103 around one pulley shaft, i.e., the pulley shaft JX1 with respect to the pitch hub 11107, and the pitch motion of the end tool 11100 includes a rotational motion of the jaw 11103 coupled to the pitch hub 11107, which occurs as the pitch hub 11107 rotates around one pulley shaft, i.e., the pulley shaft JX4 together with the end tool hub 11108.

The pitch hub 11107 may include a first hub 11107*a* and a second hub 11107*b*.

The first hub 11107*a* of the pitch hub 11107 may be connected to the jaw 11103. As an example, the first hub 11107*a* may be elongated to connect to one region of the first jaw 11101, and specifically, may have two bars that are formed side by side to face each other and coupled to each other by placing one region of the first jaw 11101 therebetween.

The second hub 11107*b* of the pitch hub 11107 may be connected to the end tool hub 11108, for example, may have two bars that are formed side by side to face each other, and may be coupled to each other by placing one region of the end tool hub 11108 therebetween.

As described above, the pulley shaft JX5 is different from one pulley shaft, i.e., the pulley shaft JX4 may be disposed in the end tool hub 11108 to be spaced apart from the pulley shaft JX4 and closer to a connection unit than the pulley shaft JX4. The pulley shaft JX4 and the pulley shaft JX5 may have axes in directions parallel to each other.

A pulley shaft JX2, which is different from the pulley shaft JX1, is disposed in the pitch hub 11107 in a direction adjacent to and parallel to the pulley shaft JX1. In addition, a pulley shaft JX3 and the pulley shaft JX4 may be formed in a direction different from (for example, intersecting or orthogonal to) the direction in which the pulley shaft JX1 and the pulley shaft JX2 are disposed, and may be sequentially disposed in a direction toward (or away from the operation member) the connection unit.

The pulley shaft JX4 may be a pitch motion shaft of the end tool 11100, and the pulley shaft JX1 may be a yaw motion shaft.

The pulley shaft JX3 and the pulley shaft JX5 may be pitch auxiliary pulley shafts, and the pulley shaft JX2 may be a yaw auxiliary pulley shaft. One or more driving wires, such as a wire configured to transmit a driving force for a pitch motion or a yaw motion may have at least one region in contact with or wound around the pulley shafts JX1, JX2, JX3, JX4, and JX5.

The pulley shafts JX2, JX3, JX5 adjacent to the pulley shaft JX4, which is a pitch motion shaft, and the pulley shaft JX1, which is a yaw motion shaft, may control paths along which the driving wires are wound around the pulley shaft JX4 and the pulley shaft JX1 to secure the efficiency of the arrangement of the driving wires and stabilize the paths for transmitting forces through the driving wires.

In addition, at least one region of the forward-moving wire 11110 may be in contact with or wound around the pulley shafts JX1, JX2, JX3, JX4, and JX5.

A more detailed description of the arrangement of the pulley shafts JX1, JX2, JX3, JX4, and JX5 will be provided below.

One or more switching pulley shafts AX1 and AX2 may be disposed in the end tool 11100, and one or more pulleys corresponding to the switching pulley shafts AX1 and AX2 may be disposed.

For example, the switching pulley shafts AX1 and AX2 may be disposed in the jaw 11103, specifically, in the proximal end 11101*p* side of the first jaw 11101, and may be disposed closer to the distal end 11101*d* of the first jaw 11101 than at least the above-described pulley shafts JX1, JX2, JX3, JX4, and JX5.

The switching pulley shafts AX1 and AX2 may be shafts formed parallel to each other, and may be disposed to have different backward and forward positions with respect to each other such that the switching pulley shaft AX1 and the switching pulley shaft AX2 are sequentially disposed with respect to the distal end 11101*d* of the first jaw 11101 and some regions of the switching pulley shaft AX1 and the switching pulley shaft AX2 are overlap each other.

The switching pulley shafts AX1 and AX2 may be regions where at least one region of the forward-moving wires 11110 is wound or comes into contact to organize and guide the path of the forward-moving wire 11110 before entering the pulley shafts JX1, JX2, JX3, JX4, and JX5. A more detailed description of the arrangement of the switching pulley shafts AX1 and AX2 will be provided below.

As shown in FIG. 22, the first forward-moving wire 11111 and the second forward-moving wire 11112 may be correspondingly wound around the first fixed pulley 11121 and the second fixed pulley 11122 in the first jaw 11101 to be redirected, and connected to the rear of the end tool 11100 via at least one region of each of the switching pulley shafts AX1 and AX2 and the pulley shafts JX1, JX2, JX3, JX4, and JX5. Furthermore, the first forward-moving wire 11111 and the second forward-moving wire 11112 may further extend to the manipulation unit via the connection unit to be precisely controlled. Accordingly, precise motion control of the operation member 11140 may be easily implemented, and details thereof will be described later.

The jaw 11103 of the end tool 11100 will be described in more detail.

FIG. 23 is a perspective view schematically illustrating the second jaw of the end tool of FIG. 18.

The second jaw 11102 may be formed in an elongated bar shape as a whole, and for example, the second jaw 11102 may be formed in a rod shape to correspond to the first jaw 11101 in at least one region.

A proximal end 11102*p* of the second jaw 11102 may include a region that is coupled to the first jaw 11101. As an example, the proximal end 11102*p* is formed to be rotatable around one shaft JX of the proximal end 11102*p* with respect to the first jaw 11101.

The second jaw 11102 may have various forms, and as a specific example, a plurality of anvil grooves may be formed in at least one region of a surface of the second jaw 11102 facing the first jaw 11101, and the anvil groove may have a shape corresponding to the shape of the staple 11530.

The anvil groove of the second jaw 11102 may serve as a support for allowing the staple 11530 to be bent when the operation member 11140 pushes and raises the staple 11530 during a staple motion.

The second jaw 11102 includes a guide groove 11102*a*. The guide groove 11102*a* may have a shape elongated in a longitudinal direction of the second jaw 11102.

The guide groove 11102*a* may be formed to guide the operation member 11140, and may be a groove formed to pass through a region facing the operation member 11140. Through this, one region of the operation member 11140, such as at least one region of the body 11142 of the operation member 11140, or a first clamp 11146 connected thereto may pass through the guide groove 11102*a* to exit to the outside of the second jaw 11102. When the operation member 11140 moves forward, the first clamp 11146 may pass through the guide groove 11102*a* of the second jaw 11102 to be exposed to the outside of the second jaw 11102, and may come into contact with an upper surface of the second jaw 11102 or apply pressure thereto. As the operation member 11140 moves, the first clamp 11146 applies pressure on the upper surface of the second jaw 11102 and a second clamp 11147 to be described later applies pressure on a lower surface of the first jaw 11101 such that a gap between the second jaw 11102 and the first jaw 11101 decreases, allowing the second jaw 11102 to naturally remain in a closed state with respect to the first jaw 11101.

FIG. 22 is a perspective view schematically illustrating the first jaw of the end tool of FIG. 21. FIG. 23 is a plan view schematically illustrating the first jaw of the end tool of FIG. 18.

Referring to FIGS. 22 and 23 and the like, the first jaw 11101 is formed in an elongated bar shape as a whole, and a rotation shaft may be disposed in the proximal end such that the first jaw 11101 is rotationally movable, and such a rotation shaft may correspond to the rotation shaft JX formed in the second jaw 11102 described above. In addition, the cartridge 11500 may be accommodated closer to the distal end 11101*d* side than the rotation shaft.

In other words, the first jaw 11101 may be formed entirely in the form of a hollow box with one surface (upper surface) thereof removed, such that a cartridge accommodation unit 11101*a* capable of accommodating the cartridge 11500 may be formed inside the first jaw 11101. That is, the first jaw 11101 may be formed in a substantially "U" shape in cross section.

A guide groove 11101*h* may be formed in a bottom surface of the first jaw 11101, the bottom surface opposite to an upper open region formed by removing one surface. Specifically, the guide groove 11101*h* may be formed to guide a linear motion of the operation member 11140.

The guide groove 11101*h* may be formed to guide the operation member 11140, and may be a groove formed to pass through a region facing the operation member 11140. Through this, one region of the operation member 11140, such as at least one region of the body 11142 of the operation member 11140, or the second clamp 11147 connected thereto may pass through the guide groove 11101*h* to exit to the outside of the first jaw 11101. When the operation member 11140 moves forward, the second clamp 11147 may pass through the guide groove 11101*h* of the first jaw 11101 to be exposed to the outside of the first jaw 11101, and may come into contact with the lower surface of the first jaw 11101 or apply pressure thereto. As the operation member 11140 moves, the second clamp 11147 applies pressure on the lower surface of the first jaw 11101 and the first clamp 11146 applies pressure on the upper surface of the second jaw 11102 such that a gap between the second jaw 11102 and the first jaw 11101 decreases, allowing the second jaw 11102 to naturally remain in a closed state with respect to the first jaw 11101.

In an optional embodiment, the first jaw 11101 may include a window 11101*b*. After operating the operation member 11140 or using the end tool 11100, the second clamp 11147 of the operation member 11140 may be located corresponding to the window 11101*b*, and the coupled state of the first jaw 11101 and the operation member 11140 may be released.

The first jaw 11101 may include the front space 11101*c* located ahead of the cartridge accommodation unit 11101*a*.

For example, the front space 11101*c* may be disposed closer to the distal end 11101*d* of the first jaw 11101 than the cartridge accommodation unit 11101*a*. The plurality of fixed pulleys 11120 may be disposed in the front space 11101*c*, for example, the first fixed pulley 11121 and the second fixed pulley 11122 may be disposed in the front space 11101*c*.

According to the above-described technical solutions of the present disclosure, in the present disclosure, based on a connection status of a second connection member, it is possible to detect whether at least one of an end tool and a connector is mounted, and based on a connection status of a first connection member, it is possible to detect whether a drape is attached, as well as to transmit and receive information about a single-use end tool.

Further, the present disclosure can provide functions of a surgical instrument by using only the minimum necessary contacts.

The effects of the present disclosure are not limited to those mentioned above, and other effects not mentioned may be clearly understood by those of ordinary skill in the art from the following description.

Each of the embodiments described above is an embodiment that can be implemented independently, but it is also possible for the structures of each embodiment to be applied to other embodiments in a combined manner.

The above-described method may be recorded as a program that may be executed on a computer, and may be implemented in a general-purpose digital computer operating the program using a computer-readable recording medium. In addition, the structure of the data used in the method described above may be recorded on a computer-readable recording medium through various means. Examples of the computer-readable recording medium include storage media such as magnetic storage media (e.g., a ROM, floppy disks, hard disks, and the like), and optical read media (e.g., CD-ROMs, DVDs, and the like).

Meanwhile, the above-described method may be included and provided in a computer program product. The computer program product may be traded as a product between a seller and a buyer. The computer program product may be distributed in the form of a machine-readable storage medium (e.g., compact disc read-only memory (CD-ROM)), or be distributed (e.g., downloaded or uploaded) online via an application store (e.g., PlayStore™), or between two user devices (e.g., smart phones) directly. When distributed online, at least a part of the computer program product may be temporarily generated or at least temporarily stored in the machine-readable storage medium, such as memory of the manufacturer's server, a server of the application store, or a relay server.

It will be understood by those skilled in the art to which the present embodiment pertains that the present disclosure may be implemented in modified forms without departing from the spirit and scope of the present disclosure. Therefore, the disclosed methods are should be considered in an illustrative aspect rather than a restrictive aspect. The scope of the present disclosure should be defined by the claims rather than the above-mentioned description, and equivalents to the claims should be interpreted to fall within the present disclosure.

What is claimed is:

1. A surgical instrument comprising:

an end tool including one or more jaws formed to be rotatable;

a handle configured to control a motion of the end tool and detect a mounting of at least one component directly or indirectly connected thereto; and a connector formed to connect between the handle and the end tool through a first connection member and a second connection member, wherein the first connection member includes one end to which a first contact of the end tool is connected and another end to which a third contact of the handle is connected, and the second connection member includes one end to which a second contact of the end tool is connected and another end to which a fourth contact and a fifth contact of the handle are connected, wherein the handle transmits and receives information about at least one of the end tool and the connector based on a connection status of the first connection member, and detects whether at least one of the end tool and the connector is mounted based on a connection status of the second connection member, wherein the first connection member is formed to extend in a direction from the handle toward the end tool, wherein the second connection member is formed to extend in the direction from the handle toward the end tool, wherein the one end and the another end of each of the first connection member and the second connection member are formed to be inclined with respect to a plane perpendicular to the direction from the handle toward the end tool.

2. The surgical instrument of claim 1, wherein the handle determines whether the connector is mounted based on a closed loop formed by each of the fourth contact and the fifth contact being connected to the second connection member.

3. The surgical instrument of claim 1, wherein the connector includes a reuse prevention unit whose structure is deformed based on a pressure generated as the connector is mounted to or detached from the handle.

4. The surgical instrument of claim 1, wherein the handle and the end tool are connected to a same ground by the second contact, the fourth contact, and the fifth contact being connected to the second connection member.

5. The surgical instrument of claim 1, wherein the information about the end tool includes at least one of a type of the end tool, a length of the end tool, whether the end tool is in use, a number of times the end tool has been used, and error information about the end tool.

6. The surgical instrument of claim 1, wherein the handle transmits at least one of details of an error, a position of at least one member included in the end tool, and a current value input to at least one motor included in the surgical instrument to the end tool, based on whether the error has occurred in the end tool.

7. The surgical instrument of claim 1, wherein the one end of the first connection member includes a sixth contact contactable with the first contact, the another end of the first connection member includes a seventh contact connected to the third contact, the one end of the second connection member includes an eighth contact contactable with the second contact, and the another end of the second connection member includes a ninth contact contactable with the fourth contact and the fifth contact.

8. The surgical instrument of claim 1, wherein the handle includes:

a sub-board disposed based on a distal end of the handle and connected to at least one of the third contact, the fourth contact and the fifth contact; and a main board connected to the sub-board and configured to control an operation of the surgical instrument.

9. The surgical instrument of claim 1, further comprising a power generation unit that includes:

a motor pack including at least one motor, which is disposed to be at least partially accommodated in a housing of the handle and generates power for driving the end tool based on a signal input to the handle; and a roll drive motor configured to generate power for roll-rotating the motor pack.

10. The surgical instrument of claim 9, further comprising a power transmission unit including at least one wire that transmits the power generated from the power generation unit to the end tool.

11. A connector formed to connect between a handle and an end tool through a first connection member and a second connection member, wherein the first connection member includes one end to which a first contact of the end tool is connected and another end to which a third contact of the handle is connected, and the second connection member includes one end to which a second contact of the end tool is connected and another end to which a fourth contact and a fifth contact of the handle are connected, wherein the first connection member is formed to extend in a direction from the handle toward the end tool, wherein the second connection member is formed to extend in the direction from the handle toward the end tool, wherein the one end and the another end of each of the first connection member and the second connection member are formed to be inclined with respect to a plane perpendicular to the direction from the handle toward the end tool.

12. The connector of claim 11, wherein the second connection member forms a closed loop by being connected to each of the fourth contact and the fifth contact.

13. The connector of claim 11, further comprising a reuse prevention unit whose structure is deformed based on a pressure generated as the connector is mounted to or detached from the handle.

14. The connector of claim 11, wherein the handle and the end tool are connected to a same ground by the second contact, the fourth contact, and the fifth contact being connected to the second connection member.

15. The connector of claim 11, wherein the one end of the first connection member includes a sixth contact contactable with the first contact, the another end of the first connection member includes a seventh contact connected to the third contact, the one end of the second connection member includes an eighth contact contactable with the second contact, and the another end of the second connection member includes a ninth contact contactable with the fourth contact and the fifth contact.

16. A method of controlling a surgical instrument, the method comprising:

detecting whether at least one of an end tool and a connector is mounted based on a connection status of a second connection member; and transmitting and receiving information about at least one of the end tool and the connector based on a connection status of a first connection member, wherein the end tool includes one or more jaws formed to be rotatable, the connector is formed to connect between a handle and the end tool through a first connection member and a second connection member, wherein the first connection member includes one end to which a first contact of the end tool is connected and another end to which a third contact of the handle is connected, and the second connection member includes one end to which a second contact of the end tool is connected and another end to which a fourth contact and a fifth contact of the handle are connected, and the handle controls a motion of the end tool and detects a mounting of one or more components directly or indirectly connected thereto, wherein the first connection member is formed to extend in a direction from the handle toward the end tool, wherein the second connection member is formed to extend in the direction from the handle toward the end tool, wherein the one end and the another end of each of the first connection member and the second connection member are formed to be inclined with respect to a plane perpendicular to the direction from the handle toward the end tool.

* * * * *